(12) United States Patent
Black et al.

(10) Patent No.: US 9,721,336 B2
(45) Date of Patent: *Aug. 1, 2017

(54) TOMOGRAPHIC IMAGING OF MULTIPHASE FLOWS

(71) Applicant: Saudi Arabian Oil Company, Dhahran (SA)

(72) Inventors: Michael John Black, Dhahran (SA); Talha Jamal Ahmad, Dhahran (SA); Mohamed Nabil Noui-Mehidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/218,737

(22) Filed: Jul. 25, 2016

(65) Prior Publication Data
US 2016/0335759 A1    Nov. 17, 2016

Related U.S. Application Data

(63) Continuation of application No. 14/595,689, filed on Jan. 13, 2015, now Pat. No. 9,424,674.

(Continued)

(51) Int. Cl.
*G06K 9/00* (2006.01)
*G06T 7/00* (2017.01)
(Continued)

(52) U.S. Cl.
CPC .............. *G06T 7/0004* (2013.01); *G01F 1/58* (2013.01); *G01F 1/66* (2013.01); *G01F 1/74* (2013.01);
(Continued)

(58) Field of Classification Search
None
See application file for complete search history.

(56) References Cited

U.S. PATENT DOCUMENTS

| 5,485,743 A | 1/1996 | Taherian et al. |
| 5,719,329 A | 2/1998 | Jepson et al. |

(Continued)

FOREIGN PATENT DOCUMENTS

| EP | 2199755 A1 | 6/2010 |
| EP | 2453230 A1 | 5/2012 |

(Continued)

OTHER PUBLICATIONS

"Handbook of Multiphase Metering", Norwegian Society for Oil and Gas Measurement/The Norwegian Society of Chartered Technical and Scientific Professionals, (2005).

(Continued)

*Primary Examiner* — Nancy Bitar
(74) *Attorney, Agent, or Firm* — Bracewell LLP; Constance G. Rhebergen; Albert B. Kimball, Jr.

(57) ABSTRACT

Tomographic reconstruction is performed of cross-sectional images of downhole or surface multiphase flows containing water (brine), oil, and gas phases. Measures are obtained of digital transmission (or analog attenuation) and also of analog transit time to form two views of the same cross sectional flow in a location of interest in a flow conduit. The measures are then merged by synthesizing a composite image of the multiphase flows. Rather than performing a complex tomographic reconstruction requiring a large number of calculations, measures are also obtained directly from the tomographic pattern which can be used to reconstruct an approximation of the cross sectional flow by the superposition of circles of variable position, radius and density representing flow patterns.

12 Claims, 11 Drawing Sheets

Related U.S. Application Data

(60) Provisional application No. 61/973,367, filed on Apr. 1, 2014.

(51) Int. Cl.

| | | |
|---|---|---|
| *G06T 11/60* | (2006.01) | |
| *G01N 29/06* | (2006.01) | |
| *G01F 1/58* | (2006.01) | |
| *G01F 1/66* | (2006.01) | |
| *G01F 1/74* | (2006.01) | |
| *G06T 7/20* | (2017.01) | |
| *G06T 11/00* | (2006.01) | |
| *G06T 7/70* | (2017.01) | |
| *G01N 22/00* | (2006.01) | |

(52) U.S. Cl.
CPC ......... *G01N 22/00* (2013.01); *G01N 29/0672* (2013.01); *G06T 7/20* (2013.01); *G06T 7/70* (2017.01); *G06T 11/008* (2013.01); *G06T 11/60* (2013.01); *G01N 2291/02433* (2013.01); *G06T 2207/10072* (2013.01); *G06T 2207/30108* (2013.01)

(56) References Cited

U.S. PATENT DOCUMENTS

| | | | | |
|---|---|---|---|---|
| 5,929,342 A | * | 7/1999 | Thompson | G01F 1/64 73/861.04 |
| 6,354,146 B1 | * | 3/2002 | Birchak | E21B 47/101 73/61.79 |
| 6,655,221 B1 | * | 12/2003 | Aspelund | G01F 1/363 73/861.04 |
| 6,758,100 B2 | | 7/2004 | Huang | |
| 7,706,986 B2 | * | 4/2010 | Frohlich | G01N 29/024 702/48 |
| 8,360,635 B2 | | 1/2013 | Huang et al. | |
| 8,576,084 B2 | * | 11/2013 | Reese | G01F 1/3209 340/606 |
| 9,031,797 B2 | | 5/2015 | Huang et al. | |
| 9,404,781 B2 | * | 8/2016 | Black | G01F 1/66 |
| 9,424,674 B2 | * | 8/2016 | Black | G06T 11/60 |
| 2002/0011120 A1 | * | 1/2002 | Huang | G01F 1/662 73/861.25 |
| 2003/0051558 A1 | | 3/2003 | Melnikov et al. | |
| 2006/0266127 A1 | | 11/2006 | Gysling et al. | |
| 2008/0163700 A1 | | 7/2008 | Huang | |
| 2009/0306911 A1 | | 12/2009 | Gysling | |
| 2011/0112773 A1 | | 5/2011 | Atkinson | |
| 2013/0086994 A1 | | 4/2013 | Noui-Mehidi | |
| 2014/0008304 A1 | | 1/2014 | Jansen et al. | |
| 2014/0331783 A1 | | 11/2014 | Xie | |

FOREIGN PATENT DOCUMENTS

| | | |
|---|---|---|
| WO | 02/077635 A2 | 10/2002 |
| WO | 2005031279 A1 | 4/2005 |
| WO | 2007129897 A1 | 11/2007 |
| WO | 2009112834 A1 | 9/2009 |
| WO | 2012087120 A1 | 6/2012 |
| WO | 2013028870 A1 | 2/2013 |

OTHER PUBLICATIONS

Avinash C. Kak, Malcolm Slaney, "Principles of Computerized Tomographic Imaging," IEEE Press, New York, USA (1988), Chaper 3,pp. 49-112.

Bishop, "Pattern Recognition and Machine Learning", Springer, Berlin, Chapter 3.3 Bayesian Linear Regression p. 152-160 (2007).

Bishop, "Pattern Recognition and Machine Learning", Springer, Berlin, Chapter 4.5 Bayesian Logistic Regression p. 217-220 (2007).

Bishop, "Pattern Recognition and Machine Learning", Springer, Berlin, Chapter 8.1 Bayesian Networks p. 360-371 (2007).

Brennen, C.E., "Fundamentals of Multiphase Flows", Cambridge University Press, Chapter 7 Flow Patterns p. 163-195 (2005).

International Search Report and Written Opinion for related PCT application PCT/US/2015/021383 dated Jul. 22, 2015.

International Search Report and Written Opinion for related PCT application PCT/US2015/021375 dated Jul. 22, 2015.

International Search Report and Written Opinion for related PCT application PCT/US2015/021419 dated Jul. 22, 2015.

International Search Report and Written Opinion for related PCT application PCT/US2015/021437 dated Jul. 22, 2015.

International Search Report and Written Opinion PCT/US2015/021371 dated Dec. 14, 2015.

H. Murrell, "Computer-Aided Tomography," The Mathematical J. V6 (1996), pp. 60-65.

H.Luo, "A Training Based No-Reference Image Quality Assessment Algorithm," Int. Conf. on Image Proc., 5 (2004) pp. 2973-2976.

Hindi, "A Noise Tolerant Fine Tuning Algorithm for the Naïve Bayesian Learning Algorithm", J. of King Saud Univ.—Comp. and Inf. Sci. 26, (2014) pp. 237-246.

L. Sirovich and M. Kirby, "Low-dimensional procedure for the characterization of human faces," J. Opt. Soc. Am A, 4 (1987), pp. 519-524.

M.H.F.Rahiman et al. "Design and modeling of ultrasonic tomography for two-component high-acoustic impedance mixture," Sens. and Act. A: Phys., 147 (2008) pp. 409-414.

M.H.F.Rahiman et al. "The Front-End Hardware Design Issue in Ultrasonic Tomography," IEEE Sens. J., 10 (2010) pp. 1276-1281.

M.H.F.Rahiman et al. "Ultrasonic Process Tomographic Imaging Sensor: An Approach Utilising Transceivers Method," Proc. of the Int. Conf. on Comp uter and Comm. Eng. (2008).

M.H.F.Rahiman et al. "Ultrasonic Transmission-Mode Tomography Imaging for Liquid/Gas Two Phase Flow," IEEE Sens. J., 6 (2006) pp. 1706-1715.

M.Turk and A. Pentland, "Eigenfaces for Face Detection/Recognition" J. Cog. Neuroscience, 3(1) (1991), pp. 71-86.

M.Turk and A. Pentland, "Face Recognition Using Eigenfaces", Proc. IEEE Conf. on Comp. Vision and Patt. Recog., (1991) pp. 586-591.

N.M.N. Ayob et al. "Ultrasound Processing Circuitry for Ultrasonic Tomography," Proc. of the Int. Conf. on Man-Machine Sys. (2009).

Press, Teukolsky, Vetterling, Filannery, "Numerical Recipes in C: The Art of Scientific Computing", Cambridge University Press, 2nd Edition Chapter 10, p. 394-455 (1992).

Von Kármán vortex shedding. Encyclopedia of Mathematics. URL:http://www.encyclopediaofmath.org/index.php?title=Von_K%C3%A1rm%C3%A1n_vortex_shedding&oldid=23554.

\* cited by examiner

TOMOGRAPHIC IMAGING OF MULTIPHASE FLOWS

CROSS-REFERENCE TO RELATED APPLICATIONS

The present application is a continuation of U.S. patent application Ser. No. 14/595,689 filed Jan. 13,2015,now U.S.Patent No. 9,424,674,which claimed priority from U.S.Provisional Application No. 61/973,367,filed Apr. 1, 2014. The present application claims priority for each of U.S. patent application Ser. No. 14/595,689 filed Jan. 13, 2015 and U.S. Provisional Application No. 61/973,367,filed Apr. 1,2014. For purposes of United States patent practice, this application incorporates the contents of each of such applications by reference in their entirety.

BACKGROUND OF THE INVENTION

1. Field of the Invention

The present invention relates to tomographic imaging of multiphase flow in conduits, and more particularly to forming images of the presence and location of oil, water (brine) and gas in flow conduits.

2. Description of the Related Art

Tomographic imaging of flow tends to focus in general on the imaging of two phases. The technique generally used for two phase flow reconstruction has been based upon what is known as the filtered back projection algorithm. This type of flow reconstruction is described for example by Kak, Avinash C., Slaney, Malcolm "*Principles of Computerized Tomographic Imaging*," IEEE Press, New York, USA (1988), and Murrell, H. "Computer-Aided Tomography," *The Mathematical J.* V6 (1996), pp. 60-65.

However, because of the nature of the fluids present in production of oil and gas, it is necessary to form images of three phase flow in conduits involved in hydrocarbon production. Because of the different fluid properties of water (brine), oil and gas it is difficult to address all three sets of fluids simultaneously. In the case of oil-water or water-oil multiphase flows, the medium has been utilized. In the case of liquid-gas or gas-liquid flows (where the liquid is brine or oil or both) an attenuation approach has been utilized. As far as is known, neither method, however, has provided a wholly satisfactory picture of a three phase multiphase flow cross section.

SUMMARY OF THE INVENTION

Briefly, the present invention provides a new and improved apparatus for forming tomographic images of three phase flow in a conduit. An array of a plurality of transmitters is mounted about the periphery of the conduit emitting energy to travel through the fluid in the conduit, and an array of a plurality of receivers mounted about the periphery of the conduit receiving energy after travel through the fluid in the conduit. The apparatus also includes a data processing system forming tomographic images of the three phase flow in the conduit. The data processing system includes a processor which forms measures of the speed of travel of the energy between individual ones of the plurality of transmitters and receivers, and also forms measures of the attenuation of the energy between individual ones of the plurality of transmitters and receivers. The data processor further forms a synthesized composite image of the relative presence and position of the three fluid phases over a cross-sectional area of the conduit based on the formed measures of the speed of travel and attenuation of the energy in the conduit. The data processing system also includes a display presenting the synthesized composite image for evaluation and analysis.

The present invention also provides a new and improved data processing system forming tomographic images of three phase flow in a conduit based on energy travel through the fluid in the conduit from an array of a plurality of receivers mounted about the periphery of the conduit to a plurality of receivers mounted about the periphery of the conduit. The data processing system includes a processor which forms of the speed of travel of the energy between individual ones of the plurality of transmitters and receivers, and further forms measures of the attenuation of the energy between individual ones of the plurality of transmitters and receivers. The processor also forms a synthesized composite image of the relative presence and position of the three fluid phases over a cross-sectional area of the conduit based on the formed measures of the speed of travel and attenuation of the energy in the conduit. A display of the data processing system presents the synthesized composite image for evaluation and analysis.

The present invention also provides a new and improved computer implemented method of forming tomographic images of three phase flow in a conduit based on energy travel through the fluid in a conduit from an array of a plurality of receivers mounted about the periphery of the conduit to a plurality of receivers mounted about the periphery of the conduit. With the computer implemented method, measures are formed of the speed of travel of the energy between individual ones of the plurality of transmitters and receivers. Measures are also formed of the attenuation of the energy between individual ones of the plurality of transmitters and receivers. The computer implemented method also forms a synthesized composite image of the relative presence and position of the three fluid phases over a cross-sectional area of the conduit based on the formed measures of the speed of travel and attenuation of the energy in the conduit, and presents the synthesized composite image for evaluation and analysis.

The present invention also provides a new and improved data storage device having stored in a non-transitory computer readable medium computer operable instructions for causing a data processing system to form tomographic images of three phase flow in in a conduit from an array of a plurality of receivers mounted about the periphery of the conduit to a plurality of receivers mounted about the periphery of the conduit. The instructions stored in the data storage device cause the data processing system to form measures of the speed of travel of the energy between individual ones of the plurality of transmitters and receivers, and also form measures of the attenuation of the energy between individual ones of the plurality of transmitters and receivers. The instructions also cause the data processing system to form a synthesized composite image of the relative presence and position of the three fluid phases over a cross-sectional area of the conduit based on the formed measures of the speed of travel and attenuation of the energy in the conduit, and to present the synthesized composite image for evaluation and analysis.

The present invention also provides a new and improved apparatus for forming tomographic images of three phase flow in a conduit, which has an array of a plurality of transmitters mounted about the periphery of the conduit emitting energy to travel through the fluid in the conduit, and an array of a plurality of receivers mounted about the periphery of the conduit receiving energy after travel through the fluid in the conduit. The apparatus also includes a data processing system which forms tomographic images of the three phase flow in the conduit. A processor of the data processing system forms measures of the speed of travel of the energy between individual ones of the plurality of transmitters and receivers, and also forms measures of the attenuation of the energy between individual ones of the plurality of transmitters and receivers. The processor further forms a geometrically reconstructed composite image of the relative presence and position of the three fluid phases over a cross-sectional area of the conduit based on the formed measures of the speed of travel and attenuation of the energy in the conduit. The data processing system also includes a display presenting the geometrically reconstructed image for evaluation and analysis.

The present invention also provides a new and improved data processing system forming tomographic images of three phase flow in a conduit based on energy travel through the fluid in the conduit from an array of a plurality of receivers mounted about the periphery of the conduit to a plurality of receivers mounted about the periphery of the conduit. The data processing system has a processor forming measures of the speed of travel of the energy between individual ones of the plurality of transmitters and receivers, and also measures of the attenuation of the energy between individual ones of the plurality of transmitters and receivers. The processor further forms a geometrically reconstructed composite image of the relative presence and position of the three fluid phases over a cross-sectional area of the conduit based on the formed measures of the speed of travel and attenuation of the energy in the conduit. A display of the data processing system presents the geometrically reconstructed composite image for evaluation and analysis.

The present invention also provides a new and improved computer implemented of forming tomographic images of three phase flow in a conduit based on energy travel through the fluid in a conduit from an array of a plurality of receivers mounted about the periphery of the conduit to a plurality of receivers mounted about the periphery of the conduit. The computer implemented method forms measures of the speed of travel of the energy between individual ones of the plurality of transmitters and receivers, and also forms measures of the attenuation of the energy between individual ones of the plurality of transmitters and receivers. The computer implemented method also forms a geometrically reconstructed composite image of the relative presence and position of the three fluid phases over a cross-sectional area of the conduit based on the formed measures of the speed of travel and attenuation of the energy in the conduit, and presents the geometrically reconstructed composite image for evaluation and analysis.

The present invention also provides a new and improved data storage device having stored in a non-transitory computer readable medium computer operable instructions for causing a data processing system to form tomographic images of three phase flow in in a conduit from an array of a plurality of receivers mounted about the periphery of the conduit to a plurality of receivers mounted about the periphery of the conduit. The instructions stored in the data storage device causing the data processing system to form measures of the speed of travel of the energy between individual ones of the plurality of transmitters and receivers, and to form measures of the attenuation of the energy between individual ones of the plurality of transmitters and receivers. The instructions also cause the data processing system to form a geometrically reconstructed composite image of the relative presence and position of the three fluid phases over a cross-sectional area of the conduit based on the formed measures of the speed of travel and attenuation of the energy in the conduit, and to present the synthesized composite image for evaluation and analysis.

The present invention also provides a new and improved apparatus for forming tomographic images of three phase flow in a conduit, including a first array of a plurality of transmitters mounted about the periphery of the conduit emitting energy at a first frequency to travel through the fluid in the conduit, and a first array of a plurality of receivers mounted about the periphery of the conduit receiving energy at the first frequency after travel through the fluid in the conduit. The apparatus also includes a second array of a plurality of transmitters mounted about the periphery of the conduit emitting energy at a second frequency to travel through the fluid in the conduit, and a second array of a plurality of receivers mounted about the periphery of the conduit receiving energy at the second frequency after travel through the fluid in the conduit. The apparatus also includes a data processing system which forms tomographic images of the three phase flow in the conduit, including a processor which forms measures of the speed of travel of the energy between individual ones of the plurality of transmitters and receivers of the first and second arrays. The processor further forms measures of the attenuation of the energy between individual ones of the plurality of transmitters and receivers of the first and second arrays. The processor forms a synthesized composite image of the relative presence and position of the three fluid phases over a cross-sectional area of the conduit based on the formed measures of the speed of travel and attenuation of the energy in the conduit. A display of the data processing system presents the synthesized composite image for evaluation and analysis.

DETAILED DESCRIPTION OF THE PREFERRED EMBODIMENTS

Tomographic Data Acquisition

Figure 1:
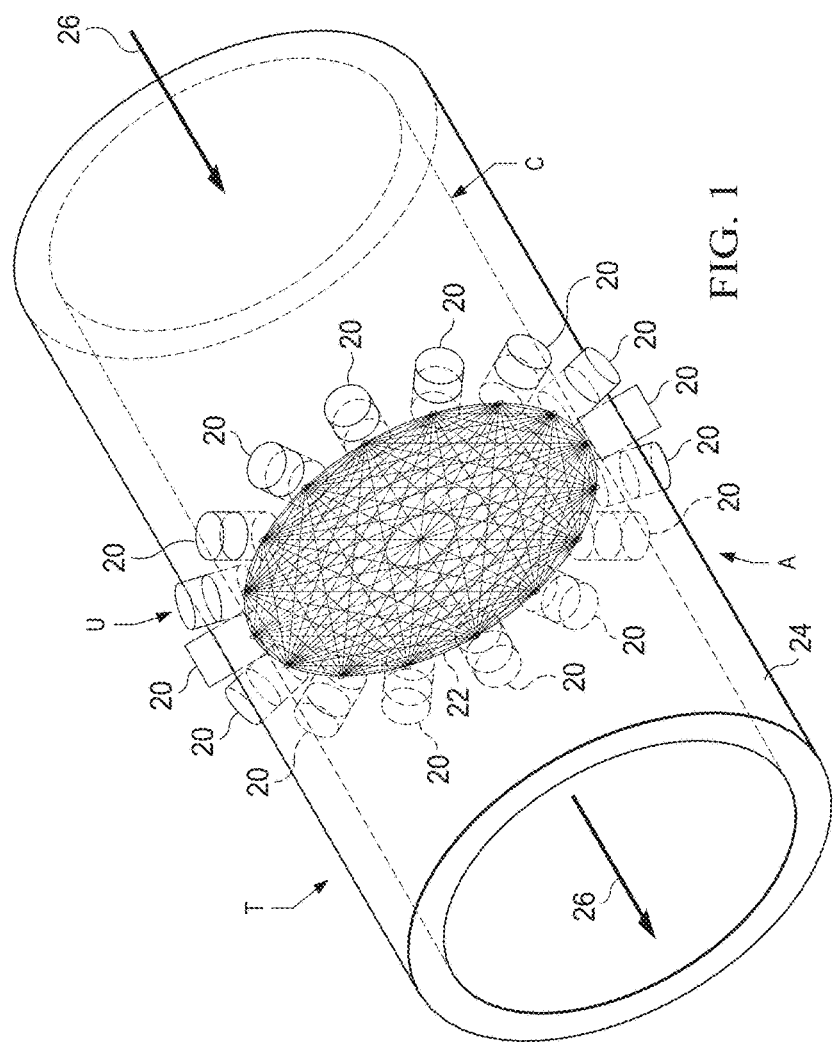
FIG. 1 is an isometric view, partially in schematic diagram form, of an ultrasonic imaging system mounted with a conduit according to the present invention.
Figure 15:
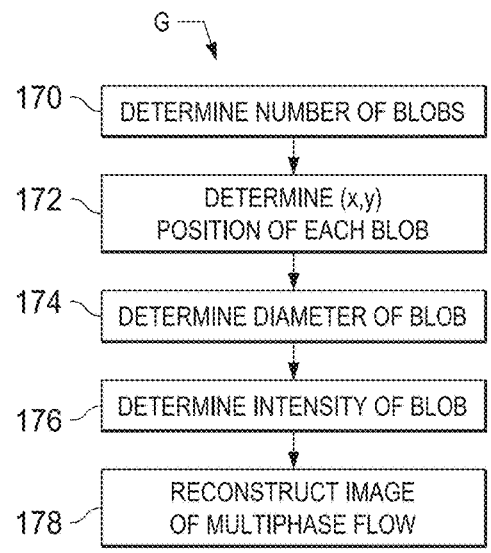
FIG. 15 is a functional block diagram of a set of steps performed in a data processing system in tomographic reconstruction of multiphase flow performed in accordance with the present invention.

Referring to FIG. 1, a tomographic system T for data acquisition of an apparatus A according to the present invention for forming tomographic images of three phase fluid flow in a conduit C is shown. The apparatus A also includes a data processing system D (FIG. 16) and methodology (FIGS. 12 and 15) which provide three-phase descriptions of multiphase mixture where in this preferred embodiment the three phases are oil, water (brine) and gas based on measurements from the tomographic system T.

The tomographic system T of the present invention takes the form of an array U of ultrasound transceivers 20 which transmit ultrasonic energy to travel through a flow conduit C, such as production tubing or other pipe. It should be understood that other conduits through which three phase (water (or brine), oil and gas) fluid flow is to be measured may also be the subject of tomographic imaging according to the present invention.

The travel of energy through the fluids in the conduit C occurs over a network of transmission channels indicated schematically at 22 where fluid properties can be measured along individual ones of the transmission channels 22 as represented as a line crossing from a transmitting transceiver 20t to a receiving transceiver 20r. The transceivers 20 are mounted in conduit C such as a length of production tubing 24. The transceiver 20 is closely coupled acoustically to the multiphase flow indicated schematically by arrows 26 which is passing through the tubing 24.

Figure 2:
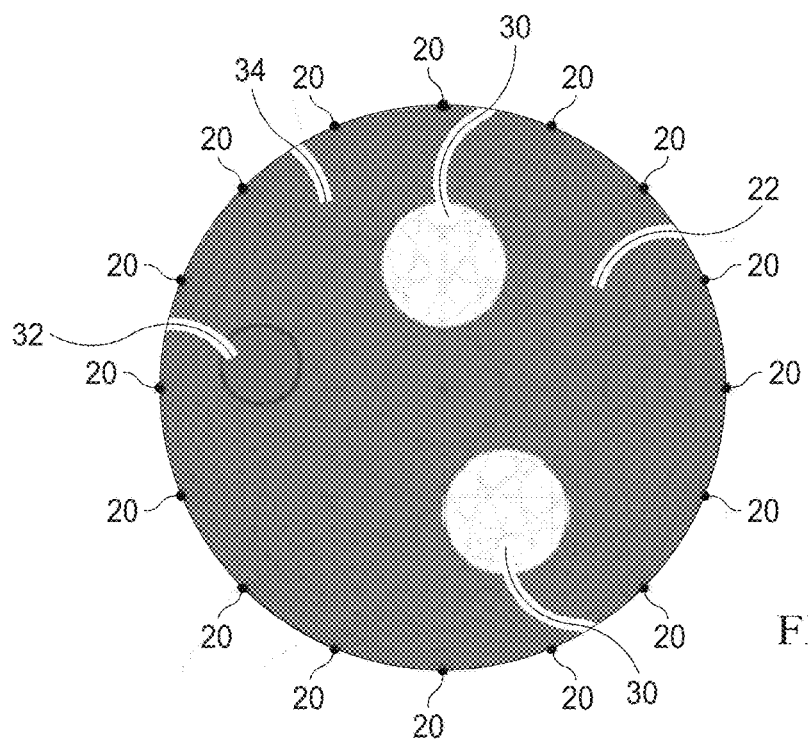
FIG. 2 is a vertical cross-section view of fluid flow through the ultrasonic imaging system of FIG. 1.

FIG. 2 illustrates a three phase liquid medium such as oil 30, a gaseous medium 32 and a continuous medium such as water or brine 34 in the production tubing 24. In typical multiphase flow, the separate phases appear in vertical cross-sectional images such as FIG. 2 as round, generally circular segments which can be referred to as blobs. It should be understood that the allocation of three phases in FIG. 2 is illustrative, and it should be noted that the allocation of fluids in FIG. 2 can vary widely depending on the nature of the multiphase flow. For example, the continuous medium can be any of gas, oil, or water (brine) depending on the flow regime. A comprehensive description of possible multiphase flow patterns is described in "The Handbook of Multiphase Metering", *Norwegian Society for Oil and Gas Measurement/The Norwegian Society of Charter Technical and Scientific Professionals* (2005), for example.

Each of the three fluids has properties relevant to transmission of ultrasonic waves as outlined in Table 1:

TABLE 1

| Fluid Parameters | | |
|---|---|---|
| | Speed of Sound (ms$^{-1}$) | Attenuation Coefficient (dB · MHz$^{-1}$ · cm$^{-1}$) |
| Oil | $c_{oil}$ | $\alpha_{oil}$ |
| Water (Brine) | $c_{water}$ | $\alpha_{water}$ |
| Gas | $c_{gas}$ | $\alpha_{gas}$ |

Generally speaking, $$c_{water} > c_{oil} > c_{gas}$$

and $$\alpha_{water} < \alpha_{oil} < \alpha_{gas}$$

Figure 3:
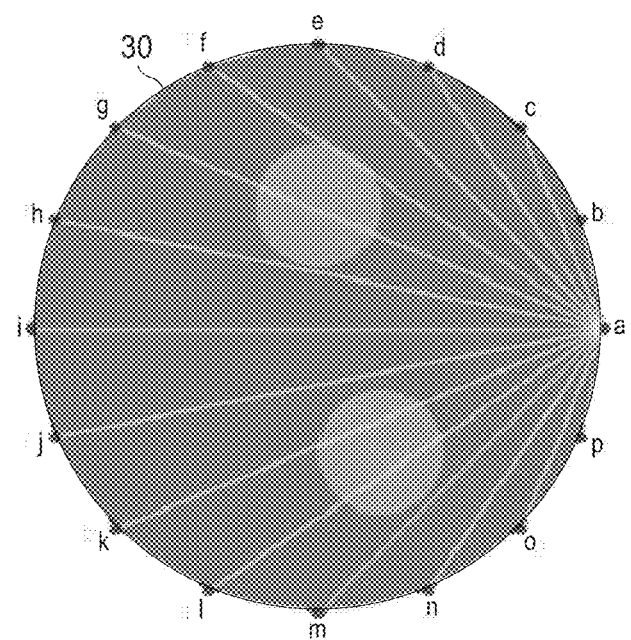
FIG. 3 is a schematic diagram of data acquisition sequencing in the ultrasonic imaging system of FIG. 1.

As shown at 22 in FIG. 1, and also in FIG. 2, the transmission channels 22 travelling from a source transceiver 20t to a receiving transceiver 20r have the potential to cross multiple fluids. At the receiver transducer 20r, a signal is measured from which an average speed or attenuation of transmitted ultrasonic energy can be measured. The resultant measurand, whether speed or attenuation, is a function of the properties of the different types of fluid crossed by the energy during its travel. Because the properties of the phases in Table 1 above are different, different fluid media are recognizable by tomographic measurement. The sequencing of the measurement is shown in FIG. 3.

In order to systematically probe the multiphase fluid it is necessary to measure every possible permutation of transducer pairs. Backward and forward measurement across the same channel is preferable as this provides a better signal to noise ratio.

In general there are N transceivers 20. FIG. 3 shows sixteen as an example with each labeled by letters from a-p, respectively. In order to make a measurement, a single transducer such as indicated at sensor a in FIG. 2 is selected to be an example emitting source. The remaining sensors (b through p, respectively) are chosen as receivers. In an example embodiment of the present invention, the transceivers 20 at each of locations a through p in FIG. 2 are sensors are 333 kHz ultrasound transducers manufactured by Pro-Wave in Taiwan which send a single square voltage pulse of duration 2.1 µs and amplitude in the 10-20V range. The pulse generates a burst of ultrasound energy which propagates out from sensor a. For each receiving sensor b through p, the arrival time and attenuation can be measured and transmitted to a data processing system D (FIG. 16) for storage and subsequent processing, as will be described.

It is to be noted that a non-uniformity correction is required for attenuation measurement because the gain of each sensor a through p may be different. This non-uniformity correction can be calculated initially for the tomographic data acquisition system T before deployment within a known homogeneous fluid such as distilled water in a test conduit or container.

Table 2 shows a potential measurement sequence for the configuration shown in FIG. 3, with TX indicating the transceiver functioning as transmitter and RX indicating the transceivers receiving the transmission.

TABLE 2

Transmission Matrix for 16 sensors, a-p.

|   | a  | b  | c  | d  | e  | f  | g  | h  | i  | j  | k  | l  | m  | n  | o  | p  |
|---|----|----|----|----|----|----|----|----|----|----|----|----|----|----|----|----|
| a | TX | RX | RX | RX | RX | RX | RX | RX | RX | RX | RX | RX | RX | RX | RX | RX |
| b | RX | TX | RX | RX | RX | RX | RX | RX | RX | RX | RX | RX | RX | RX | RX | RX |
| c | RX | RX | TX | RX | RX | RX | RX | RX | RX | RX | RX | RX | RX | RX | RX | RX |
| d | RX | RX | RX | TX | RX | RX | RX | RX | RX | RX | RX | RX | RX | RX | RX | RX |
| e | RX | RX | RX | RX | TX | RX | RX | RX | RX | RX | RX | RX | RX | RX | RX | RX |
| f | RX | RX | RX | RX | RX | TX | RX | RX | RX | RX | RX | RX | RX | RX | RX | RX |
| g | RX | RX | RX | RX | RX | RX | TX | RX | RX | RX | RX | RX | RX | RX | RX | RX |
| h | RX | RX | RX | RX | RX | RX | RX | TX | RX | RX | RX | RX | RX | RX | RX | RX |
| i | RX | RX | RX | RX | RX | RX | RX | RX | TX | RX | RX | RX | RX | RX | RX | RX |
| j | RX | RX | RX | RX | RX | RX | RX | RX | RX | TX | RX | RX | RX | RX | RX | RX |
| k | RX | RX | RX | RX | RX | RX | RX | RX | RX | RX | TX | RX | RX | RX | RX | RX |
| l | RX | RX | RX | RX | RX | RX | RX | RX | RX | RX | RX | TX | RX | RX | RX | RX |
| m | RX | RX | RX | RX | RX | RX | RX | RX | RX | RX | RX | RX | TX | RX | RX | RX |
| n | RX | RX | RX | RX | RX | RX | RX | RX | RX | RX | RX | RX | RX | TX | RX | RX |
| o | RX | RX | RX | RX | RX | RX | RX | RX | RX | RX | RX | RX | RX | RX | TX | RX |
| p | RX | RX | RX | RX | RX | RX | RX | RX | RX | RX | RX | RX | RX | RX | RX | TX |

In practice the measurement sequences can be performed through each individual channel 22 either through sending a single pulse through a transmitting or TX transceiver and receiving simultaneously through multiple receive (RX) channels. Alternatively, if the number of measurement channels on the measurement device is smaller than the number of receive or RX channels, then multiple pulses can be sent by the transmitter as data is gathered from a subset of receivers. In an extreme case, this can have a pulse is sent by the transmitter for each individual receiver or RX measurement. There may be advantages to this, such as in cases where there is coupling between receive channels either acoustically or electrically.

Generalizing to N sensors, Table 2 shows that there are $N^2-N$ individual transmission channels between sensors: in the example where there are sixteen sensors there are 240 channels. For each channel there is a corresponding reverse channel. Full coverage is necessary as this provides better signal to noise ratio in the final tomographic reconstruction.

In the following description, the declaration of the following variables applies.

N=number of sensors
R=radius of pipe (distance from transceiver to central axis of pipe at (0, 0))
m∈{0, ..., N−1}=index of transmitting transceiver $$\Delta\beta = \frac{2\pi}{N} =$$

angular separation between adjacent transceivers (relative to (0, 0))

$$\alpha = \frac{\pi}{N} = \text{angular separation between adjacent transmission channels}$$

β=m·Δβ=angular position of transmitter measured relative to x-axis $$\frac{(-N)}{2} < n < \frac{N}{2},$$

where n is the index of the transmission channel

γ=nα=channel angle, measured relative to a line between (R cos β, R sin β) and (0, 0)

The received measurands whether they be time of flight (average speed) or amplitude can be presented in the format shown in Table 3 using N=16 and the geometry of the system is shown in FIG. 4.

TABLE 3

Matrix for Arranging Measurements from Tomographic Data Gathering

| | | γ | | | | | | | | | | | | | |
|---|---|---|---|---|---|---|---|---|---|---|---|---|---|---|---|
| | | −78.75 | −67.50 | −56.25 | −45.00 | −33.75 | −22.50 | −11.25 | 0.00 | 11.25 | 22.50 | 33.75 | 45.00 | 56.25 | 67.50 | 78.75 |
| β | 0.0 | | | | | | | | | | | | | | | |
| | 22.5 | | | | | | | | | | | | | | | |
| | 45.0 | | | | | | | | | | | | | | | |
| | 67.5 | | | | | | | | | | | | | | | |
| | 90.0 | | | | | | | | | | | | | | | |
| | 112.5 | | | | | | | | | | | | | | | |
| | 135.0 | | | | | | | | | | | | | | | |
| | 157.5 | | | | | | | | | | | | | | | |
| | 180.0 | | | | | | | | | | | | | | | |
| | 202.5 | | | | | | | | | | | | | | | |
| | 225.0 | | | | | | | | | | | | | | | |
| | 247.5 | | | | | | | | | | | | | | | |
| | 270.0 | | | | | | | | | | | | | | | |
| | 292.5 | | | | | | | | | | | | | | | |
| | 315.0 | | | | | | | | | | | | | | | |
| | 337.5 | | | | | | | | | | | | | | | |

In the embodiment described above, ultrasound transceivers are described and utilized for tomographic data acquisition. However, it should be understood that other measurement mechanisms and technologies may be utilized according to the present invention for tomographic data acquisition, such as:

(a) replacing transceivers with transmitter receiver pairs; or (b) parameter measurement mechanisms such as capacitance, electromagnetic wave absorption, radioactive attenuation or other mechanism where energy is transferred through multiple fluid media and the transmission properties of the media influence the propagation of the energy in a manner indicative of the presence and location of multiphase fluids in a conduit.

Multiphase Flow Tomography Simulation

During step 100 (FIG. 13), the geometry of the cross sectional flow of fluid through the tubing 24 is defined. This is done with the following declaration of variables to correspond to the geometry displayed in FIG. 4.

Radius of pipe centered on origin or center line
Number of blobs and their respective radii
Number of transducers
Speed of sound in water—$c_{water}$
Speed of sound in air—$c_{air}$
Speed of sound in oil—$c_{oil}$
Angular separation of transducers
Angular separation between rays measured relative to sensor origin This is an implementation of the geometry described in FIG. 4. Here speeds of sounds for water and air are included and the position of circular blobs within the continuous medium (which can be air or water) is defined. Note that the inclusion of a second set of blobs relating to oil with an additional speed of sound for oil requires a definition of a second set of blobs with a speed of sound for oil associated for them in the 1000-1500 ms-1 range, depending on the composition of the oil.

Figure 5:
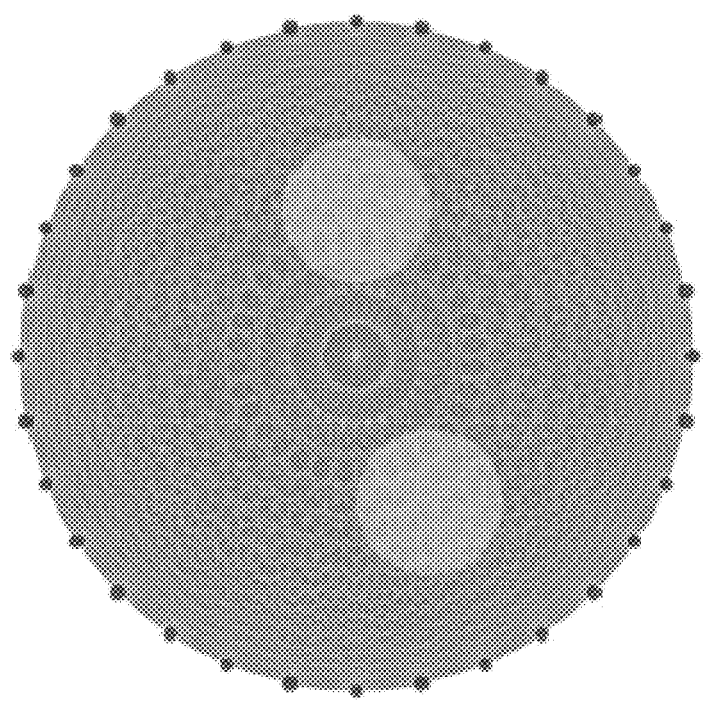
FIG. 5 is a schematic diagram of multiphase flow in the ultrasonic imaging system of FIG. 1.

The methodology of acquisition of tomographic data and its processing for determining speed of sound in the multiphase fluid in the tubing or conduit 24 is also performed for attenuation. Attenuation of the signals during travel through the multiphase fluids is measured and recorded and then processed and utilized in the same manner as speed of sound data. Step 102 is the formation by the data processing system D of an output display of the defined geometry resulting from step 100, and FIG. 5 is an example display or visualization of an example defined geometry with an numbers of blobs of the type described in connection with FIG. 2 again being present.

The above procedure of defining and visualizing geometry such as shown in FIG. 2 can be generalized with the present invention to an unspecified number of phases and a larger, unspecified number of blobs per phase, where each set of blobs can be defined as a series of circles with arbitrary position within the pipe and arbitrary and independent radii for each blob.

Using the data layout described in connection with steps 100 and 102, in step 104 the data processing system D computes or determines the distances of each transmission channel. This is required for both attenuation and speed of sound measurements. An example 15×16 output matrix (for a 16 transducer system) which maps on to Table 4 is shown below. The rows of the matrix represent different transducers and the columns represent m ·Δβ as defined above.

This equates to calculating the expression 2R cos γ, as follows:

TABLE 4

| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
|---|---|---|---|---|---|---|---|---|---|---|---|---|---|---|
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |
| 8.97415 | 17.6034 | 25.5562 | 32.5269 | 38.2476 | 42.4985 | 45.1161 | 46. | 45.1161 | 42.4985 | 38.2476 | 32.5269 | 25.5562 | 17.6034 | 8.97415 |

Table 4 displays the length of each transmission channel in a 16 transceiver system where the pipe diameter is 46 mm. Each row represents an individual transmitter specified by β and each column specifies a different channel angle specified by γ.

During step 106, the data processing system D calculates the time of travel from transmitter TX to receiver RX assuming only that a continuous medium is present. Time of flight is calculated by dividing the distance matrix above by the speed of sound in water, $c_{water}$. Correspondingly, attenuation is calculated with the expression like $e^{-\alpha_{water} x}$ where x is the length of the channel and $\alpha_{water}$ is the attenuation coefficient expressed in units of $m^{-1}$. An example output from the speed of sound calculation is shown below, with units in microseconds assuming a speed of sound in water of 1500 $ms^{-1}$.

$$\begin{pmatrix}
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277 \\
5.98277 & 11.7356 & 17.0375 & 21.6846 & 25.4984 & 28.3323 & 30.0774 & 30.6667 & 30.0774 & 28.3323 & 25.4984 & 21.6846 & 17.0375 & 11.7356 & 5.98277
\end{pmatrix}$$

In step 108, the data processing system D calculates the change in transit time (or attenuation) caused by the presence of multiphase impurities. Note that this step can be repeated multiple times to address an arbitrary number of different phases with different acoustic properties. For simplicity a single step is described assuming time of flight calculations. By replacing the equation as shown in step 106 it is possible to perform the same calculation using attenuation coefficients to calculate the change in attenuation caused by the presence of impurities.

Initially during step 108, the geometry associated with the set of blobs which define the non-continuous medium within the multiphase flow is defined. This initial stage of step 108 defines the equation of the straight line of the transmission channel in the form:

$$s(r,\gamma,t)=m(\gamma)t+c(r,\gamma)$$

This involves rotating the x-y axis by an angle $-\beta$ to create the (t, s) so that the t-axis is in line with the line between the origin and the transceiver positioned at angle $\beta$. r is the radius of the pipe, and $\gamma$ is as previously defined.

Each blob representing one segment of a phase of multiphase flow in conduit 24 is described during step 108 by an equation of a circle centered on the position (tb,sb) with radius rb. Essentially the equation of the circle can be considered as a quadratic equation and by solving the simultaneous equation of the transmission channel line and the blob circle, two roots are achieved which results in two points in (t, s) space. If these coordinates are real, then the difference between them represents the transit distance through the blob made by the intersecting transmission channel. Specifically, high and low roots for t are first calculated which are then inserted into the equation of the straight line to determine the final coordinates.

The second stage of step 108 involves the data processing system D populating a matrix similar to that generated in step 106 with time differences to those calculated in step 106.

A matrix is generated with N-1 columns and N rows are defined with each element equal to zero, where N is the number of ultrasonic transducers. A for loop is defined to increment from a value of i ranging from 1 to N, which is used to index the rows of the matrix. A second for loop (inside the first one) is defined to increment from a value of j ranging from 1 to N-1, which is used to index the columns of the matrix. A third for loop (inside the first two) is defined to increment from a value k ranging from 1 to Nblobs where Nblobs is the number of circular blobs contained within the tomographic cross section. Inside the flow loops and referring to FIG. 4, the absolute angle of the sensor position, $\beta$, is calculated by multiplying the index (i-1) by the angular separation $\Delta\beta$. The angle $\gamma$, which is the angle of the transmission channel from source to receiver measured relative to the line drawn between the origin and the position of the transmitter at angle $\beta$, is calculated by multiplying the index (j-1) by the angular separation of rays a also shown in FIG. 4. For each of the circular blobs in the simulation, a matrix of Nblob rows is defined containing for each row xblob (the k-th blob x position), yblob (the k-th blob y position) and rblob (the k-th blob radius) is defined. For each k in the central loop, each of these parameters is extracted from the blob matrix and hence the xb, yb, and rb parameters are known. To simplify the geometry of the problem, the coordinate space is rotated through an angle $-\beta$ into a (t,s) frame of reference so that the position of the source is in line with one of the axes so that the co-ordinates (xb,yb) are transformed into the point (tb,sb). A line is projected from the source at an angle $\gamma$ to the axis and the length of the chord which intersects the circular blob is determined through trigonometric relationships. This process is repeated for each blob in the simulation, and a cumulative total of chord distances is maintained at each of the elements of the original matrix with N rows and N-1 columns. Each row represents a different source transmitter with angular position $\beta$ and each column represents one of N-1 transmission channels emanating from said source measured at an angle $\gamma=n\alpha$ to the line defined between the origin and the position of the source shown in FIG. 4A. The value of each element within the matrix represents the total distance of traversed blobs made by the transmission channel—if no blobs are crossed by the channel then this will have an element value of zero. This value is called the blob transit distance.

Having defined the blob transit distance as a function of $\beta$, $\gamma$, sb, yb and rb, the two outer loops define the values of $\beta$ and $\gamma$. The central loop (k) walks through the different number of blobs and cumulatively adds their transit distances. A value is only added if the transmission channel crosses the particular blob in question. Since the blobs are defined by (x,y) coordinates, they are transformed into (t,s) coordinates by rotating through an angle $-\beta$. The output from this is a distance.

During step 110, the data processing system D determines or calculates an attenuation matrix. As described above, the attenuation can be calculated by changing to the attenuation equation previously described. To implement attenuation cumulatively the output is modified to a product rather than a sum.

For calculating a time of flight correction, the transit distances are multiplied by the following term:

$$\left(\frac{1}{c_{blob}} - \frac{1}{c_{continuous}}\right)$$

Such an approach can be applied for an arbitrary number of blob phases with different properties.

An example output from this calculation is shown below.

$$\begin{pmatrix}
0. & 0. & 0. & 0. & 22.2528 & 20.8618 & 0. & 0. & 0. & 23.5459 & 10.6525 & 0. & 0. & 0. & 0. \\
0. & 0. & 0. & 0. & 18.6744 & 22.0427 & 0. & 0. & 0. & 22.9475 & 19.0137 & 0. & 0. & 0. & 0. \\
0. & 0. & 0. & 0. & 0. & 23.5765 & 0. & 0. & 15.2078 & 23.5459 & 19.0137 & 0. & 0. & 0. & 0. \\
0. & 0. & 0. & 0. & 0. & 15.3523 & 20.8181 & 15.2122 & 23.0902 & 22.1753 & 10.6525 & 0. & 0. & 0. & 0. \\
0. & 0. & 0. & 0. & 0. & 2.36611 & 42.8664 & 23.6364 & 20.37 & 2.36611 & 0. & 0. & 0. & 0. & 0. \\
0. & 0. & 0. & 0. & 10.6525 & 22.1753 & 23.0902 & 38.5498 & 0. & 0. & 0. & 0. & 0. & 0. & 0. \\
0. & 0. & 0. & 0. & 19.0137 & 23.5459 & 15.2078 & 16.7134 & 18.5871 & 0. & 0. & 0. & 0. & 0. & 0. \\
0. & 0. & 0. & 0. & 19.0137 & 22.9475 & 0. & 0. & 23.1095 & 0. & 0. & 0. & 0. & 0. & 0. \\
0. & 0. & 0. & 0. & 10.6525 & 23.5459 & 0. & 0. & 11.6929 & 22.5825 & 0. & 0. & 0. & 0. & 0. \\
0. & 0. & 0. & 0. & 0. & 22.1753 & 15.2078 & 0. & 0. & 22.9475 & 14.5177 & 0. & 0. & 0. & 0. \\
0. & 0. & 0. & 0. & 0. & 2.36611 & 23.0902 & 0. & 0. & 20.8618 & 21.6738 & 0. & 0. & 0. & 0. \\
0. & 0. & 0. & 0. & 0. & 0. & 20.37 & 15.2122 & 0. & 22.0427 & 22.2528 & 0. & 0. & 0. & 0. \\
0. & 0. & 0. & 0. & 0. & 0. & 0. & 23.6364 & 20.8181 & 23.5765 & 18.6744 & 0. & 0. & 0. & 0. \\
0. & 0. & 0. & 0. & 0. & 0. & 18.5871 & 38.5498 & 42.8664 & 15.3523 & 0. & 0. & 0. & 0. & 0. \\
0. & 0. & 0. & 0. & 14.5177 & 22.5825 & 23.1095 & 16.7134 & 23.0902 & 2.36611 & 0. & 0. & 0. & 0. & 0. \\
0. & 0. & 0. & 0. & 21.6738 & 22.9475 & 11.6929 & 0. & 15.2078 & 22.1753 & 0. & 0. & 0. & 0. & 0.
\end{pmatrix}$$

Step 112 involves the data processing system D calculating the final transit time by adding the matrix from step 106 from the matrix to the results of step 110. For attenuation, this would be a multiplication of individual matrix elements on a 1 to 1 basis. Example results of final transit times in microseconds are shown in the example below.

$$\begin{pmatrix}
5.98277 & 11.7356 & 17.0375 & 21.6846 & 47.7512 & 49.1941 & 30.0774 & 30.6667 & 30.0774 & 51.8782 & 36.1509 & 21.6846 & 17.0375 & 11.7356 & 5.98277 \\
5.98277 & 11.7356 & 17.0375 & 21.6846 & 44.1729 & 50.375 & 30.0774 & 30.6667 & 30.0774 & 51.2799 & 44.5121 & 21.6846 & 17.0375 & 11.7356 & 5.98277 \\
5.98277 & 11.7356 & 17.0375 & 21.6846 & 25.4984 & 51.9089 & 30.0774 & 30.6667 & 45.2852 & 51.8782 & 44.5121 & 21.6846 & 17.0375 & 11.7356 & 5.98277 \\
5.98277 & 11.7356 & 17.0375 & 21.6846 & 25.4984 & 43.6846 & 50.8955 & 45.8789 & 53.1676 & 50.5076 & 36.1509 & 21.6846 & 17.0375 & 11.7356 & 5.98277 \\
5.98277 & 11.7356 & 17.0375 & 21.6846 & 25.4984 & 30.6984 & 72.9438 & 54.303 & 50.4474 & 30.6984 & 25.4984 & 21.6846 & 17.0375 & 11.7356 & 5.98277 \\
5.98277 & 11.7356 & 17.0375 & 21.6846 & 36.1509 & 50.5076 & 53.1676 & 69.2164 & 30.0774 & 28.3323 & 25.4984 & 21.6846 & 17.0375 & 11.7356 & 5.98277 \\
5.98277 & 11.7356 & 17.0375 & 21.6846 & 44.5121 & 51.8782 & 45.2852 & 47.3801 & 48.6645 & 28.3323 & 25.4984 & 21.6846 & 17.0375 & 11.7356 & 5.98277 \\
5.98277 & 11.7356 & 17.0375 & 21.6846 & 44.5121 & 51.2799 & 30.0774 & 30.6667 & 53.187 & 28.3323 & 25.4984 & 21.6846 & 17.0375 & 11.7356 & 5.98277 \\
5.98277 & 11.7356 & 17.0375 & 21.6846 & 36.1509 & 51.8782 & 30.0774 & 30.6667 & 41.7703 & 50.9148 & 25.4984 & 21.6846 & 17.0375 & 11.7356 & 5.98277 \\
5.98277 & 11.7356 & 17.0375 & 21.6846 & 25.4984 & 50.5076 & 45.2852 & 30.6667 & 30.0774 & 51.2799 & 40.0161 & 21.6846 & 17.0375 & 11.7356 & 5.98277 \\
5.98277 & 11.7356 & 17.0375 & 21.6846 & 25.4984 & 30.6984 & 53.1676 & 30.6667 & 30.0774 & 49.1941 & 47.1722 & 21.6846 & 17.0375 & 11.7356 & 5.98277 \\
5.98277 & 11.7356 & 17.0375 & 21.6846 & 25.4984 & 28.3323 & 50.4474 & 45.8789 & 30.0774 & 50.375 & 47.7512 & 21.6846 & 17.0375 & 11.7356 & 5.98277 \\
5.98277 & 11.7356 & 17.0375 & 21.6846 & 25.4984 & 28.3323 & 30.0774 & 54.303 & 50.8955 & 51.9089 & 44.1729 & 21.6846 & 17.0375 & 11.7356 & 5.98277 \\
5.98277 & 11.7356 & 17.0375 & 21.6846 & 25.4984 & 28.3323 & 48.6645 & 69.2164 & 72.9438 & 43.6846 & 25.4984 & 21.6846 & 17.0375 & 11.7356 & 5.98277 \\
5.98277 & 11.7356 & 17.0375 & 21.6846 & 40.0161 & 50.9148 & 53.187 & 47.3801 & 53.1676 & 30.6984 & 25.4984 & 21.6846 & 17.0375 & 11.7356 & 5.98277 \\
5.98277 & 11.7356 & 17.0375 & 21.6846 & 47.1722 & 51.2799 & 41.7703 & 30.6667 & 45.2852 & 50.5076 & 25.4984 & 21.6846 & 17.0375 & 11.7356 & 5.98277 \\
\end{pmatrix}$$

For attenuation this would be, as described, a product rather than a sum.

During step 114 the data processing system D calculates the average speed—this is achieved by dividing the individual matrix elements from step 112 by the distance matrix for the channels described in step 104, resulting in the following example matrix which is the same format as Table 4 and is expressed in units of ×1000 ms−1.

$$\begin{pmatrix}
1.5 & 1.5 & 1.5 & 1.5 & 0.800977 & 0.863894 & 1.5 & 1.5 & 1.5 & 0.819197 & 1.058 & 1.5 & 1.5 & 1.5 & 1.5 \\
1.5 & 1.5 & 1.5 & 1.5 & 0.865862 & 0.843642 & 1.5 & 1.5 & 1.5 & 0.828755 & 0.859263 & 1.5 & 1.5 & 1.5 & 1.5 \\
1.5 & 1.5 & 1.5 & 1.5 & 1.5 & 0.1818713 & 1.5 & 1.5 & 0.996266 & 0.819197 & 0.859263 & 1.5 & 1.5 & 1.5 & 1.5 \\
1.5 & 1.5 & 1.5 & 1.5 & 1.5 & 0.972847 & 0.886446 & 1.00264 & 0.848564 & 0.841427 & 1.058 & 1.5 & 1.5 & 1.5 & 1.5 \\
1.5 & 1.5 & 1.5 & 1.5 & 1.5 & 1.38439 & 0.618505 & 0.847098 & 0.89432 & 1.38439 & 1.5 & 1.5 & 1.5 & 1.5 & 1.5 \\
1.5 & 1.5 & 1.5 & 1.5 & 1.058 & 0.841427 & 0.848564 & 0.664582 & 1.5 & 1.5 & 1.5 & 1.5 & 1.5 & 1.5 & 1.5 \\
1.5 & 1.5 & 1.5 & 1.5 & 0.859263 & 0.819197 & 0.996266 & 0.970872 & 0.927084 & 1.5 & 1.5 & 1.5 & 1.5 & 1.5 & 1.5 \\
1.5 & 1.5 & 1.5 & 1.5 & 0.859263 & 0.828755 & 1.5 & 1.5 & 0.848255 & 1.5 & 1.5 & 1.5 & 1.5 & 1.5 & 1.5 \\
1.5 & 1.5 & 1.5 & 1.5 & 1.058 & 0.819197 & 1.5 & 1.5 & 1.0801 & 0.834697 & 1.5 & 1.5 & 1.5 & 1.5 & 1.5 \\
1.5 & 1.5 & 1.5 & 1.5 & 1.5 & 0.841427 & 0.996266 & 1.5 & 1.5 & 0.828755 & 0.955806 & 1.5 & 1.5 & 1.5 & 1.5 \\
1.5 & 1.5 & 1.5 & 1.5 & 1.5 & 1.38439 & 0.848564 & 1.5 & 1.5 & 0.863894 & 0.810809 & 1.5 & 1.5 & 1.5 & 1.5 \\
1.5 & 1.5 & 1.5 & 1.5 & 1.5 & 1.5 & 0.89432 & 1.00264 & 1.5 & 0.843642 & 0.800977 & 1.5 & 1.5 & 1.5 & 1.5 \\
1.5 & 1.5 & 1.5 & 1.5 & 1.5 & 1.5 & 0.847098 & 0.886446 & 0.818713 & 0.865862 & 1.5 & 1.5 & 1.5 & 1.5 & 1.5 \\
1.5 & 1.5 & 1.5 & 1.5 & 1.5 & 1.5 & 0.927084 & 0.664582 & 0.618505 & 0.9722847 & 1.5 & 1.5 & 1.5 & 1.5 & 1.5 \\
1.5 & 1.5 & 1.5 & 1.5 & 0.955806 & 0.834697 & 0.848255 & 0.970872 & 0.848564 & 1.38439 & 1.5 & 1.5 & 1.5 & 1.5 & 1.5 \\
1.5 & 1.5 & 1.5 & 1.5 & 0.810809 & 0.828755 & 1.0801 & 1.5 & 0.996266 & 0.841427 & 1.5 & 1.5 & 1.5 & 1.5 & 1.5
\end{pmatrix}$$

It is to be noted that the speed of sound of the continuous medium (water) is 1.5 in these units.

Figure 6:
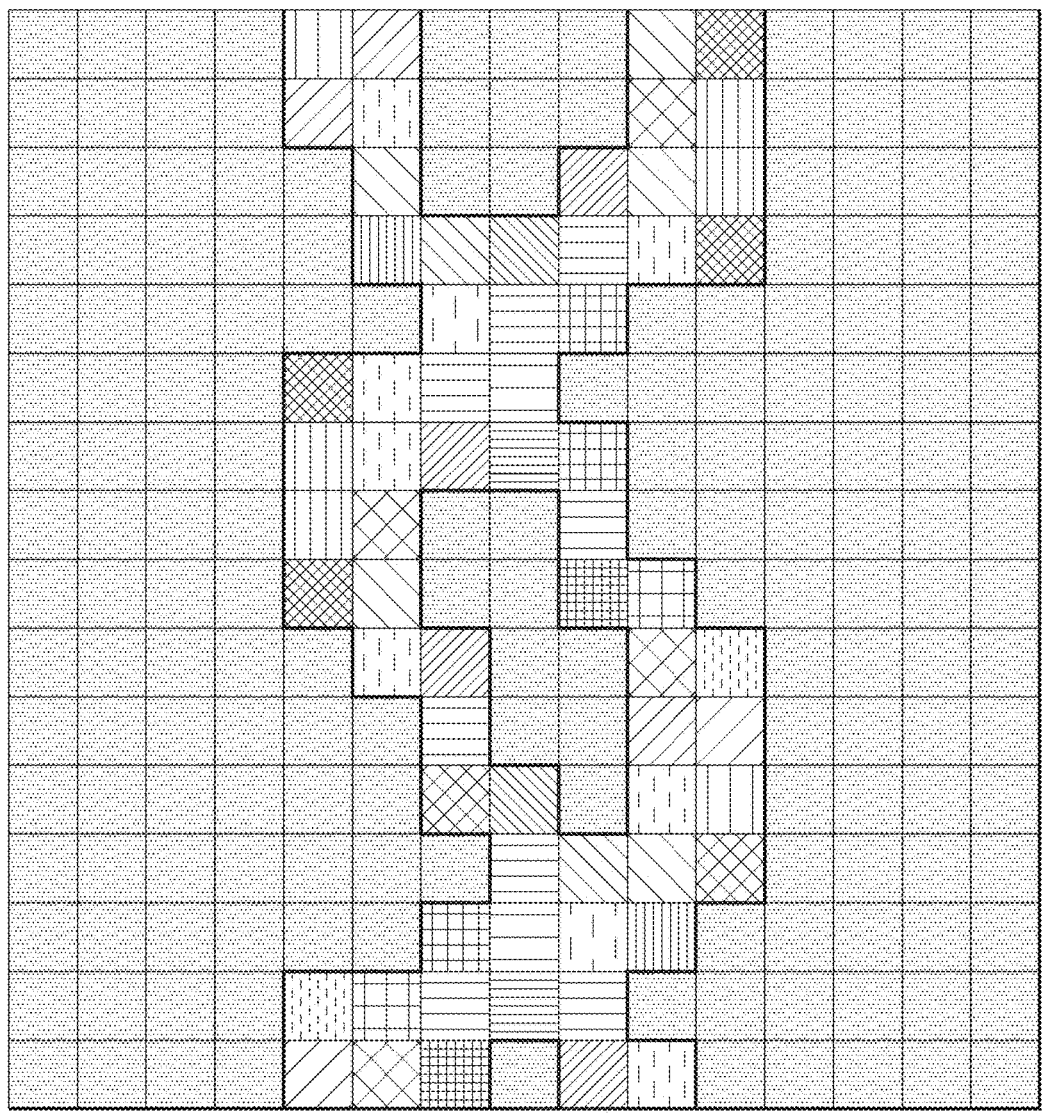
FIG. 6 is an example plot graphically illustrating patterns for data representing speed of sound obtained from ultrasonic imaging of two phase fluid flow.

FIG. 6 is a density plot showing graphically the pattern of the transmitted data for 16 channels. Each column in the sound density plot of FIG. 6 corresponds with an angle γ and each row corresponds with an angle β. It can thus be seen that the present invention provides the ability to simulate multiphase flow cross sectional patterns using an arbitrary array of transducers together with an arbitrarily complex flow cross section pattern.

Figure 7:
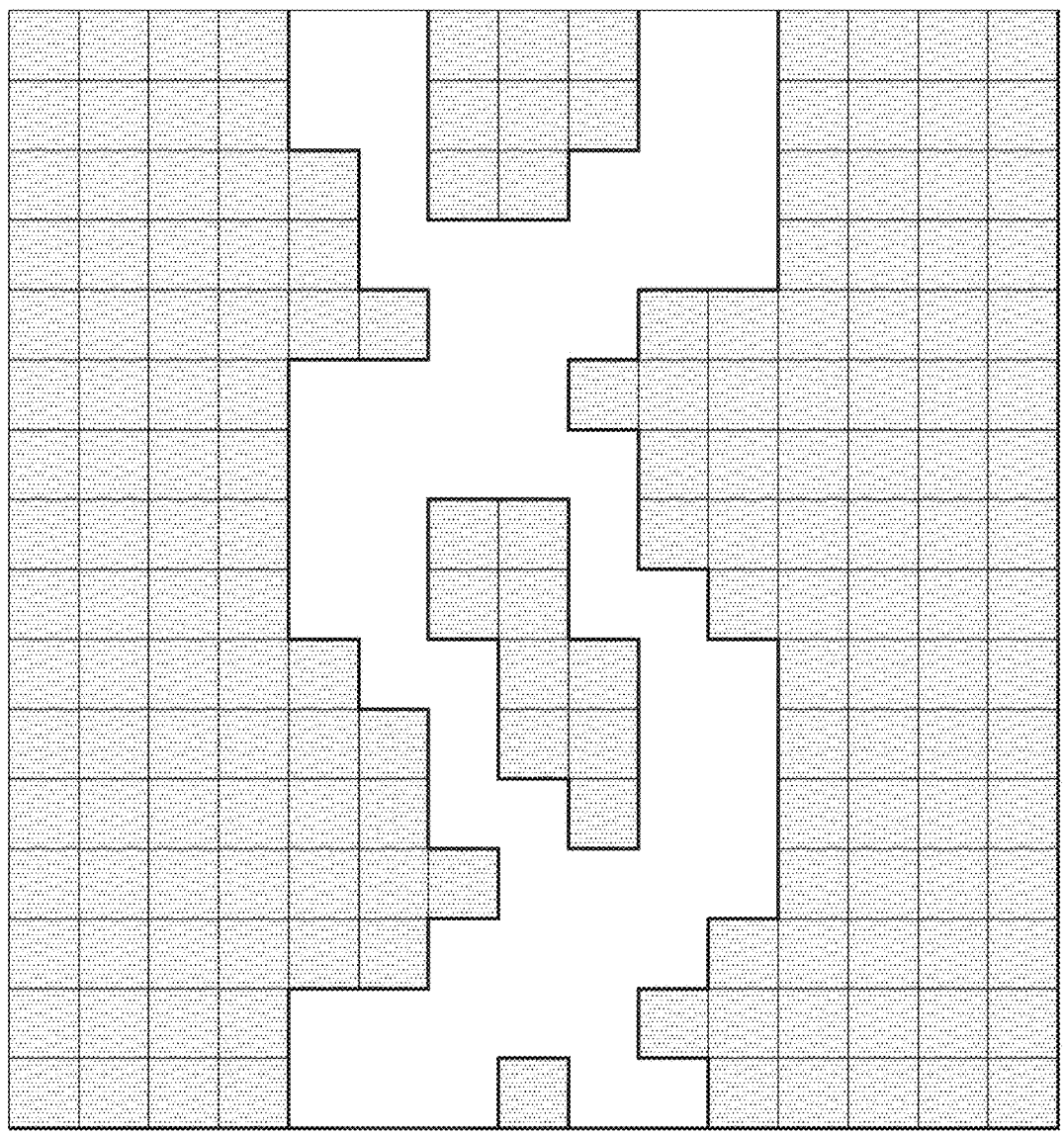
FIG. 7 is an example plot graphically illustrating patterns for data representing attenuation obtained from ultrasonic imaging of two phase fluid flow.

For attenuation calculations, assuming high attenuation of the blobs, the result is shown in FIG. 7. As was the case in FIG. 6, each column in the attenuation plot of FIG. 7 corresponds with an angle γ and each row corresponds with an angle β. The blobs have been assigned values so that they appear very opaque, but are presented in FIGS. 6 and 7 as cross-hatched segments.

3 Phase Flow Reconstruction Algorithm

During step 116, the data processing system D normalizes the tomographic image data. In cases where the input data is a speed of sound matrix resulting from step 114, the normalized data is them multiplied by a factor R cos γ.

The same normalization computation is also performed on a homogeneous speed matrix assuming only a presence of water or brine (or whatever the continuous medium is) with a fixed speed of sound of 1500 ms$^{-1}$. This allows normalization of the tomographic image which is provided according to the present invention. Normalization has been found to be of particular importance when the number of sensors is constrained, for example by small pipe diameters in downhole deployments.

An example output matrix from the speed of sound matrix is shown below:

$$\begin{pmatrix}
6.73062 & 13.2026 & 19.1672 & 24.3952 & 15.3177 & 18.3571 & 33.8371 & 34.5 & 33.8371 & 17.4073 & 20.2329 & 24.3952 & 19.1672 & 13.2026 & 6.73062 \\
13.2026 & 19.1672 & 24.3952 & 15.3177 & 16.5586 & 17.9267 & 33.8371 & 34.5 & 33.8371 & 17.6104 & 16.4324 & 24.3952 & 19.1672 & 13.2026 & 6.73062 \\
19.1672 & 24.3952 & 28.6857 & 16.5586 & 17.397 & 33.8371 & 22.4738 & 34.5 & 22.4738 & 17.4073 & 16.4324 & 24.3952 & 19.1672 & 13.2026 & 6.73062 \\
24.3952 & 28.6857 & 28.6857 & 17.9267 & 20.6723 & 19.9965 & 19.142 & 23.0607 & 19.9965 & 17.8797 & 20.2329 & 24.3952 & 19.1672 & 13.2026 & 6.73062 \\
28.6857 & 28.6857 & 28.6857 & 17.397 & 29.4171 & 13.9523 & 20.1741 & 19.4833 & 13.9523 & 29.4171 & 28.6857 & 24.3952 & 19.1672 & 13.2026 & 6.73062 \\
28.6857 & 28.6857 & 20.2329 & 20.6723 & 17.8797 & 19.142 & 33.8371 & 15.2854 & 19.142 & 31.8738 & 28.6857 & 24.3952 & 19.1672 & 13.2026 & 6.73062 \\
28.6857 & 20.2329 & 16.4324 & 29.4171 & 17.4073 & 22.4738 & 20.9132 & 22.3301 & 22.4738 & 31.8738 & 28.6857 & 24.3952 & 19.1672 & 13.2026 & 6.73062 \\
20.2329 & 16.4324 & 16.4324 & 17.8797 & 17.6104 & 33.8371 & 19.135 & 34.5 & 33.8371 & 31.8738 & 28.6857 & 24.3952 & 19.1672 & 13.2026 & 6.73062 \\
16.4324 & 20.2329 & 17.4073 & 17.4073 & 17.8797 & 33.8371 & 24.365 & 34.5 & 33.8371 & 17.7367 & 28.6857 & 24.3952 & 19.1672 & 13.2026 & 6.73062 \\
20.2329 & 17.4073 & 17.8797 & 17.8797 & 29.4171 & 22.4738 & 33.8371 & 34.5 & 22.4738 & 17.6104 & 18.2786 & 24.3952 & 19.1672 & 13.2026 & 6.73062 \\
17.4073 & 17.8797 & 28.6857 & 28.6857 & 29.4171 & 19.142 & 33.8371 & 34.5 & 19.142 & 18.3571 & 15.5057 & 24.3952 & 19.1672 & 13.2026 & 6.73062 \\
17.8797 & 28.6857 & 28.6857 & 31.8738 & 31.8738 & 20.1741 & 33.8371 & 23.0607 & 20.1741 & 17.9267 & 15.3177 & 24.3952 & 19.1672 & 13.2026 & 6.73062 \\
28.6857 & 28.6857 & 28.6857 & 31.8738 & 31.8738 & 33.8371 & 19.9965 & 19.4833 & 33.8371 & 17.397 & 16.5586 & 24.3952 & 19.1672 & 13.2026 & 6.73062 \\
28.6857 & 28.6857 & 28.6857 & 31.8738 & 31.8738 & 20.9132 & 19.9523 & 15.2854 & 20.9132 & 20.6723 & 28.6857 & 24.3952 & 19.1672 & 13.2026 & 6.73062 \\
28.6857 & 28.6857 & 18.2786 & 17.7367 & 17.7367 & 19.135 & 13.9523 & 22.3301 & 19.135 & 29.4171 & 28.6857 & 24.3952 & 19.1672 & 13.2026 & 6.73062 \\
24.3952 & 18.2786 & 15.5057 & 17.6104 & 17.6104 & 24.365 & 19.142 & 34.5 & 24.365 & 17.8797 & 28.6857 & 24.3952 & 19.1672 & 13.2026 & 6.73062 \\
\end{pmatrix}$$

An example output matrix from the homogeneous speed calculation is shown below:

$$\begin{pmatrix} 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \\ 6.73062 & 13.2026 & 19.1672 & 24.3952 & 28.6857 & 31.8738 & 33.8371 & 34.5 & 33.8371 & 31.8738 & 28.6857 & 24.3952 & 19.1672 & 13.2026 & 6.73062 \end{pmatrix}$$

In step 118 the data processing system D determines a function which is referred to as $g(n\alpha)$. An example of the determination of a $g(n\alpha)$ function is contained described in Kak, Avinash C., Slaney, Malcolm "*Principles of Computerized Tomographic Imaging*," IEEE Press, New York, USA (1988), previously cited.

During step 120 the data processing system D implements a Hamming Filter which acts to reduce spatial image noise. Because the sensor numbers are low compared to normal tomography systems, in the present example, the size of the filter is limited to 2 to minimize smearing. Hamming Filters are also described in Kak, Avinash C., Slaney, Malcolm "Principles of Computerized Tomographic Imaging," IEEE Press, New York, USA (1988), previously cited.

Step 122 includes the data processing system D padding with zeros the matrices to the left and right with a matrix with N rows and an arbitrary number of columns (nominally N) generated in step 116. This is done so the double convolution next to be performed associated with $g(n\alpha)$ and the Hamming filter has enough space to be performed.

As mentioned, the data processing system D during step 124 performs a double convolution with $g(n\alpha)$ and the Hamming filter. The $g(n\alpha)$ convolution is performed first, and the Hamming filter is performed second. Once the double convolution is performed, the padding cells added in step 122 are stripped out. The convolution is performed on both the output matrices from step 116.

An example output for the speed of sound matrix is shown below:

| | | | | | | | | | | | | | | |
|---|---|---|---|---|---|---|---|---|---|---|---|---|---|---|
| 83.7273 | 145.017 | 200.48 | 220.059 | 216.66 | 250.169 | 313.002 | 353.912 | 311.528 | 260.361 | 231.956 | 233.693 | 201.402 | 146.603 | 83.7748 |
| 83.7114 | 145.41 | 200.625 | 223.185 | 219.908 | 251.666 | 311.964 | 353.017 | 311.118 | 250.168 | 218.57 | 222.76 | 200.525 | 145.359 | 83.6602 |
| 83.9987 | 148.172 | 203.101 | 256.818 | 262.384 | 281.415 | 310.532 | 323.625 | 269.129 | 217.982 | 215.424 | 220.248 | 200.073 | 143.682 | 83.4015 |
| 82.9668 | 145.691 | 201.989 | 252.545 | 264.905 | 249.738 | 235.413 | 233.638 | 223.54 | 213.929 | 226.148 | 227.974 | 199.4 | 142.798 | 82.2264 |
| 83.7585 | 145.271 | 205.413 | 253.791 | 289.734 | 265.318 | 232.694 | 213.499 | 254.028 | 281.453 | 290.986 | 254.922 | 205.524 | 145.527 | 83.8315 |
| 81.5241 | 144.194 | 199.72 | 229.933 | 225.763 | 217.037 | 207.812 | 248.231 | 296.193 | 329.404 | 298.39 | 259.473 | 205.052 | 147.988 | 84.0684 |
| 82.0107 | 142.197 | 199.544 | 218.183 | 213.06 | 211.378 | 235.234 | 244.689 | 269.864 | 293.85 | 297.591 | 255.577 | 205.579 | 146.583 | 84.5781 |
| 83.5364 | 143.928 | 201.8 | 222.164 | 220.3 | 247.649 | 312.64 | 317.382 | 301.681 | 295.305 | 301.622 | 257.125 | 207.546 | 147.766 | 85.9198 |
| 83.695 | 145.6 | 201.259 | 233.7 | 231.774 | 259.187 | 309.566 | 330.479 | 279.642 | 259.275 | 261.618 | 255.856 | 203.114 | 147.994 | 83.9533 |
| 83.9362 | 147.724 | 203.094 | 255.067 | 261.574 | 253.996 | 273.115 | 324.395 | 309.287 | 253.607 | 225.148 | 227.765 | 200.835 | 144.768 | 83.6346 |
| 85.5599 | 147.68 | 206.81 | 256.457 | 294.537 | 286.206 | 294.739 | 316.689 | 313.795 | 247.59 | 218.722 | 219.587 | 201.565 | 143.632 | 83.6107 |
| 84.7359 | 147.69 | 205.932 | 256.92 | 298.139 | 295.452 | 272.134 | 278.166 | 280.126 | 243.157 | 213.419 | 218.701 | 199.981 | 143.453 | 82.3442 |
| 84.5178 | 148.158 | 205.603 | 259.361 | 299.655 | 330.131 | 308.364 | 264.805 | 220.922 | 208.033 | 212.457 | 219.522 | 199.33 | 143.179 | 81.7732 |
| 83.7642 | 145.571 | 204.822 | 255.417 | 295.68 | 291.288 | 248.782 | 198.755 | 195.864 | 232.572 | 263.196 | 251.698 | 202.201 | 144.953 | 82.041 |
| 82.0469 | 142.119 | 199.682 | 222.251 | 219.569 | 207.551 | 223.161 | 229.857 | 255.569 | 278.851 | 289.949 | 254.119 | 204.688 | 145.881 | 84.1542 |
| 83.3384 | 142.469 | 199.812 | 216.555 | 212.71 | 217.833 | 273.877 | 295.812 | 270.743 | 250.48 | 261.158 | 253.387 | 202.88 | 146.726 | 83.8564 |

An example output for the homogeneous matrix is shown below:

$$\begin{pmatrix}
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161 \\
82.2161 & 150.041 & 209.71 & 263.529 & 307.477 & 340.595 & 360.759 & 367.769 & 360.759 & 340.595 & 307.477 & 263.529 & 209.71 & 150.041 & 86.2161
\end{pmatrix}$$

Step 126 performed by the data processing system D requires an interpolation of each row of the above matrices to compute values for arbitrary $\gamma$. This may be, for example, done by fitting polynomial curves of order 3 to the data points. This allows estimation, for a given fixed and quantized $\beta = m \cdot \Delta\beta$, of a continuous value of $\gamma$.

Polynomial curve fitting may, however, be computationally intensive in some cases. Alternative forms of interpolation with more efficient and less computationally intensive reconstruction techniques which may be used include the following:

(a) replacing the polynomial interpolation with a linear interpolation;

(b) for a given $\gamma$, selecting the nearest value corresponding with a quantized $n\alpha$ value; or (c) if $\gamma \neq n\alpha$, then averaging adjacent values.

Figure 4A:
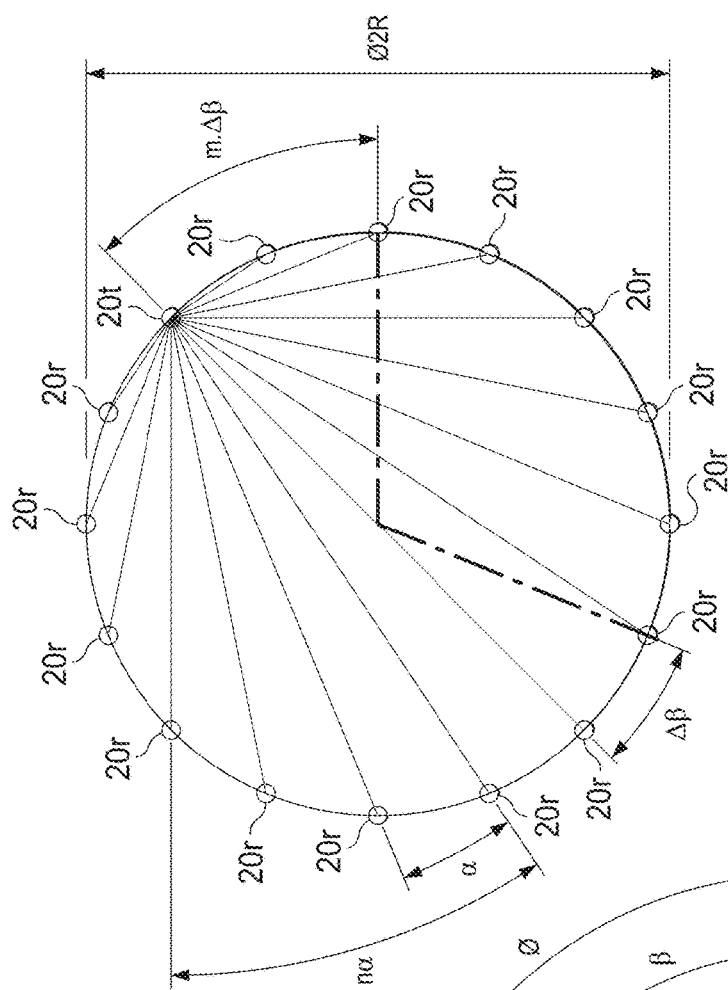
FIGS. 4A and 4B are schematic diagrams of definitions of geometric variables for the ultrasonic imaging system of FIG. 1.
Figure 4B:
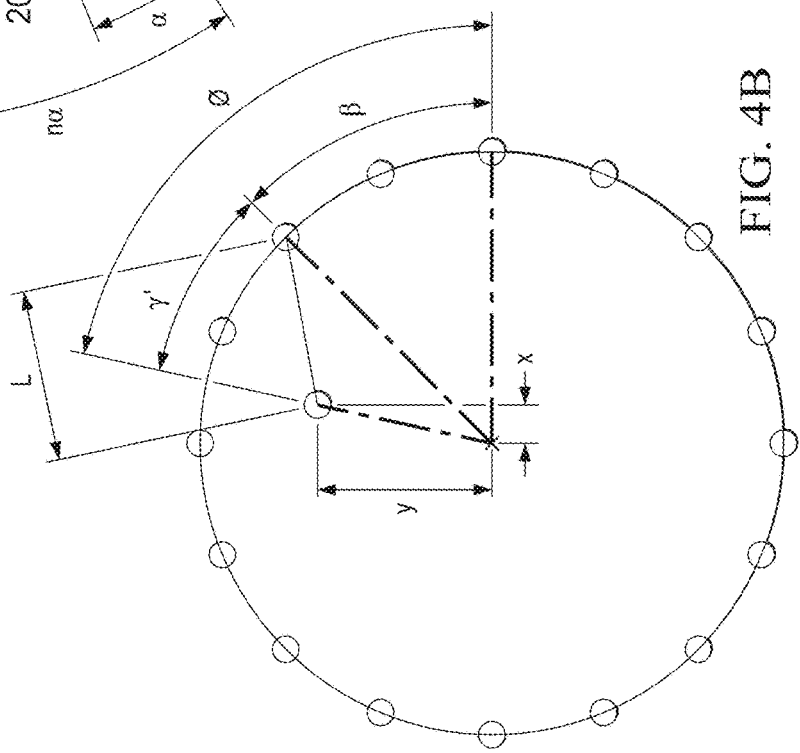

During step 128, the data processing system D first calculates a distance, L, between a point (x,y) and a given transceiver defined by $\beta = m \cdot \Delta\beta$. It then goes on to calculate an angle $\phi(x,y) \in (-\pi, \pi]$ which is the angle between the x-axis and a line between the origin and the point (x,y). Following this calculation, the data processing system D in step 128 computes the angle $\gamma'$ which is the angle between the line between the origin and the transducer, and the line between (x,y) and the transducer. It is analogous to $\gamma$ as shown in FIG. 4A except that (x,y) can be anywhere within the pipe rather than being fixed at a transceiver position. Finally the data processing system D in step 128 computes a sum which is an approximation to a Fourier transform, to transform the matrices outputted by step 124 (both the speed of sound matrix and the homogeneous matrix) into a real space plot of the measured parameter as a function of position (either attenuation or speed of sound). The dimensions in this are shown in FIG. 4B.

Figure 8:
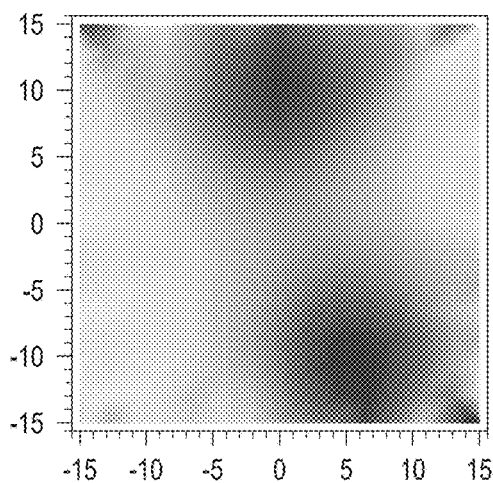
FIG. 8 is a tomographic reconstruction image of the multiphase flow of FIG. 5 obtained after filtering according to the present invention.

The data processing system D in step 130 plots the data, where the output from the speed of sound matrix is divided by the homogenous matrix on an element by element basis. This provides a flatter response to account for the limited filtering allowable with a small number of sensors. The output from this is shown in FIG. 8.

The present several differences over conventional filtered back projection of conventional tomographic image filtered back projection reconstruction. These improve the computation processing which can be applied to speed of sound, attenuation or other physically measured parameters through tomography. The geometry of the tomographic data acquisition with the present invention is different from the filtered back projection in that sensors and receivers are on the outside of a circle. The filtered back projection applies for a source at the origin and sensors around the circumference of the circle. The processing has been developed with the present invention to account for this.

Figure 9A:
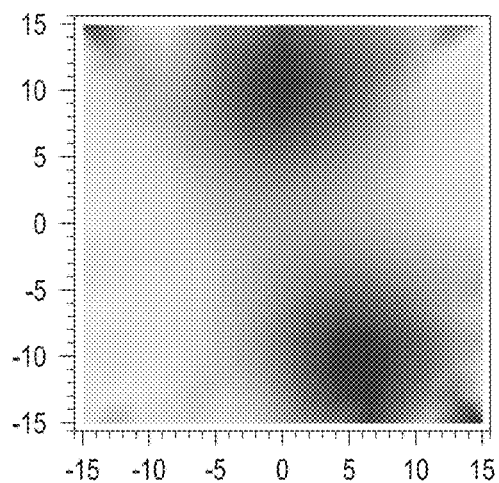
FIG. 9A is an image of normalized response obtained from the image of FIG. 8.
Figure 9B:
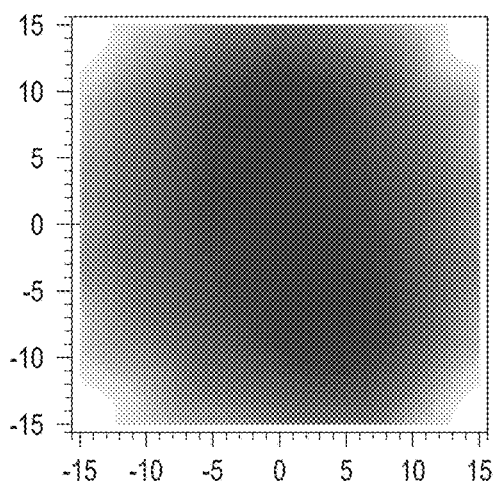
FIG. 9B is an image of un-normalized response obtained from the image of FIG. 8.

With the present invention, a relatively low number of sensors may be present in comparison to the number of inputs usually processed with a Hamming filter. When this is the case, the size of the filter can be limited, or even removed completely. In these cases. Hamming filtering may be replaced with a flattening technique where a homogenous response is calculated using the continuous medium alone, and the reconstructed response normalized against the calculated homogeneous response. FIG. 9A shows an example reconstructed response for a small number of sensors with such normalization, and FIG. 9B an example reconstructed response without normalization for comparison. The response of FIG. 9B can be seen to be swamped by background. If the response of FIG. 9B is filtered, features of interest in the data are likely to be removed.

The present invention also improves the efficiency of interpolation by using linear, nearest neighbor and adjacent element averaging for interpolation. As mentioned, in some cases, it is possible to omit the filtering performed in steps 118 through 124 and apply a direct reconstruction of the matrices during step 116, relying on the normalization to provide flattening of the response.

Figure 10:
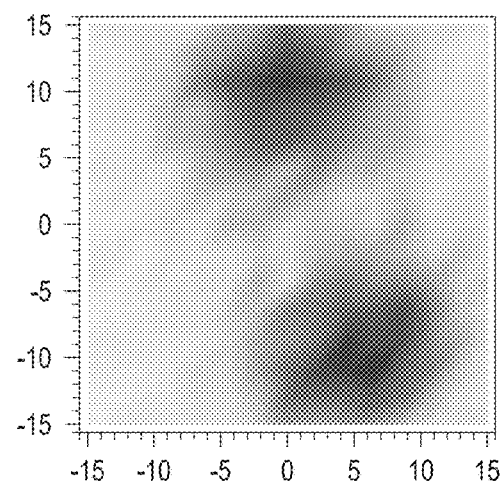
FIG. 10 is an image of an unfiltered, un-normalized response obtained from the image of FIG. 8.

In other cases, it is also possible to perform no filtering and no normalization with minimal interpolation as described, applying only a nearest neighbor technique. Output from this is obtained significantly more efficiently than the conventional two phase flow simulation. FIG. 10 is an analog output image display of results obtained from unfiltered, un-normalized processing with such nearest neighbor interpolation. The major features of multiphase flow can be seen in the image of FIG. 10 formed with such interpolation when compared with the image of FIG. 8 after more computationally intense processing.

Figure 11:
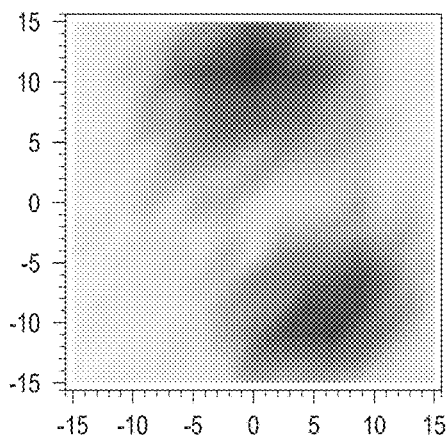
FIG. 11 is an image of an unfiltered, un-normalized response with interpolation obtained from the image of FIG. 8.

In some cases, it is also preferable to threshold the matrices obtained from step 116 into a digital format. A digital version of the analog data shown in FIG. 10 is shown in FIG. 11. The data after a threshold is applied requires reduced bandwidth for data transmission.

The present invention also contemplates a successive or iterative reconstruction processing approach which assesses the quality of the final image and applies increasingly more computation with more complex reconstruction techniques to achieve better quality images when necessary.

3 Phase Reconstruction by Synthesization

Figure 12:
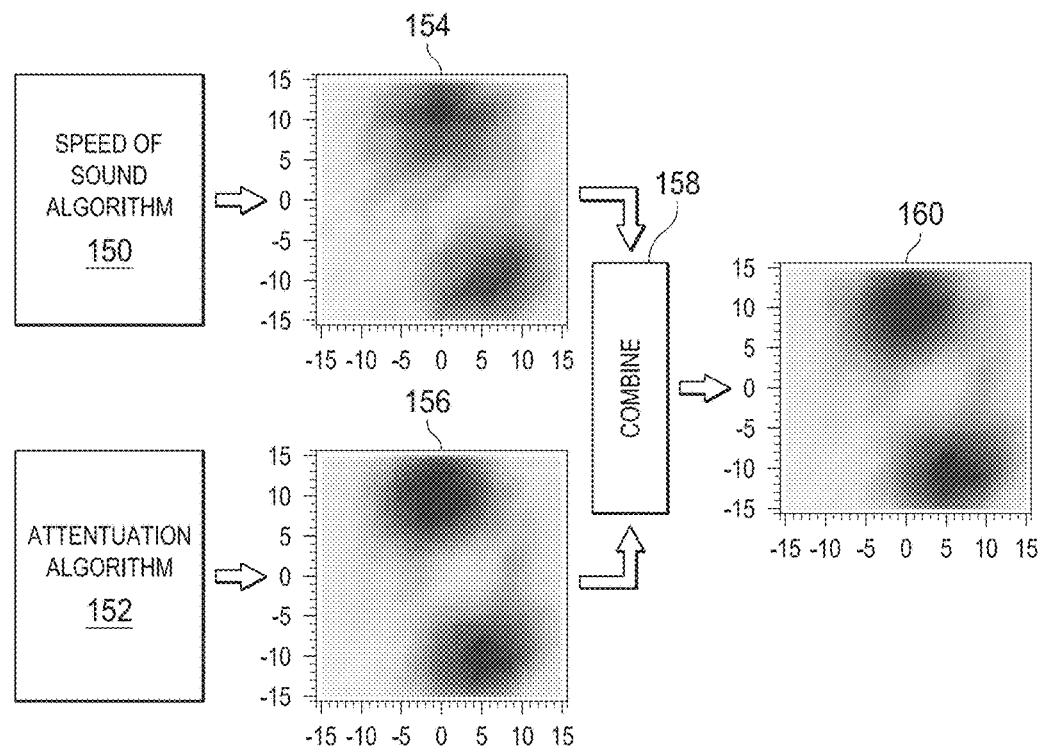
FIG. 12 is a functional block diagram of a set of steps performed in tomographic data acquisition for imaging of multiphase flow performed in accordance with the present invention.

The tomographic data acquired and processed according to the techniques of FIG. 12 are well suited for the reconstruction of 2 phase multiphase flow. However, so far as is known, although they have not been successfully applied to 3 phase flow with acceptable levels of performance.

Accordingly, with the present invention, 3 phase reconstruction methodology has been developed from which a composite image is synthesized. With such a composite image, the presence and location of three phase flow in conduits is provided for analysis and evaluation. The tomographic image data acquired according to the techniques of FIG. 12 are processed in parallel to generate two images, one based on speed of sound measurement and a second based on attenuation measurement. Once the two images representing the processing results are produced, the data can be processed to form a composite image where the two sets of data are combined. This can be done either through averaging the data or by inserting each image into a different color space, so that it can be visualized as a red-green-blue or RGB image where two of the color planes are occupied.

The 3 phase reconstruction by synthesization process for this is shown schematically at R in FIG. 12. The reconstruction process R involves a reconstruction algorithm 150 based on a speed of sound matrix (FIG. 6) which can for example provides better data for oil-water or water-oil flow. It also involves a reconstruction algorithm 152 based on an attenuation matrix (FIG. 7) which can for example provide better data for gas-liquid or liquid-gas flows. The reconstruction algorithms utilized can be any of those described in connection with FIG. 12. The reconstruction process R could also include multiple implementations of parallel algorithms 150 and 152 either adaptively or in parallel if this were considered advantageous.

The speed of sound algorithm 150 results in an output in the form of a speed of sound plot as indicated at 1204, while the attenuation algorithm 152 results in an output in the form of an attenuation plot as indicated at 156. The data forming images 154 and 156 are fed into a combining step 158 performed in the data processing system D which as a first step will include normalization of the output images. The combination performed during step 158 can take one of several forms. The data values for the two images 154 and 156 can be averaged together. Alternatively, an image quality assessment can be performed as indicated at 160, the image quality of each image 154 and 156 scored. Another alternative for step 158 is to perform a weighted average of each image in the data processing system D.

The image quality assessment 160 is performed as a function of spatial position for each image and an element by element ratio calculation performed of the ratio between qualities. The results are used to reconstruct an average image where the weighting of the average is a function of position.

Another form of reconstruction is by forming a color image where for example the speed of sound data inhabits the R plane and the attenuation inhabits the G plane. This provides a false color or pseudo-color image for human interpretation which helps to differentiate the different phases.

Efficient Geometric Reconstruction

So far, the processing techniques have relied on a computationally intensive reconstruction process which includes a summing term which approximates a Fourier transform. This sum needs to be performed for every pixel in the final image. Taking 16 sensors as an example, the summing requires 16 computations potentially including intensive interpolation functions and computational expensive floating point operations such as trigonometric functions. To create a 100×100 pixel image would require 160,000 calculations of this type to reconstruct the image.

Looking to the patterns in FIGS. 6 and 7, the presence of circular blobs generates a geometric pattern which is fully definable as follows:

$$\gamma(x, y, R, \beta) = \tan^{-1}\left(\frac{x\sin\beta - y\cos\beta}{x\cos\beta + y\sin\beta + R}\right)$$

This means that the (x,y) position of a blob can be determined by geometric analysis of the plots shown in FIGS. 6 and 7 where the midpoint of the trace is tracked and fitted either to the equation above or an approximation such as a Taylor expansion.

By analyzing the width of a track, it is possible to determine the diameter of a blob. By analyzing the intensity of the trace, it is possible to determine the property of a particular blob. The present invention also includes a geometric reconstruction methodology as indicated at G in FIG. 15, which assumes the multiphase flow consists of a superposition of circular blobs as indicated in FIG. 2.

The geometric reconstruction assumes the multiphase flow pattern is indicated by a superposition of a fixed number of circles. Rather than performing a complex tomographic reconstruction requiring a large number of calculations, the geometric reconstruction extracts measurands (the quantities or parameters to be measured) directly from the tomographic pattern which can be used to reconstruct an approximation of the cross sectional flow by the superposition of circles of variable position, radius and density.

The geometric reconstruction process G includes the data processing system D determining in step 170 a number of blobs by counting the maximum number of peaks detected in a given β row. In the case of FIGS. 6 and 7 this would be 2 blobs. In step 172, an (x,y) position of each blob is determined by fitting the above equation (or approximation) to the center point of the blob trace. During step 174, a diameter of each blob is determined by analyzing maximum angle subtended by blob (thickness of trace). Step 176 involves a determination of intensity of the various blobs by sampling intensity of trace values. During step 178, an image of multiphase flow is reconstructed using the (x,y) positions, diameters, and intensities determined by the above process.

The geometric reconstruction process can be used to produce cleaner results with fewer sensors. It should be noted that there may not be a 1 to 1 correspondence between density and actual value. However, it is possible to account for different values for different phases and a look up table can be deployed to identify different phases such as oil, water or gas.

Two Channel Tomography System

Figure 13:
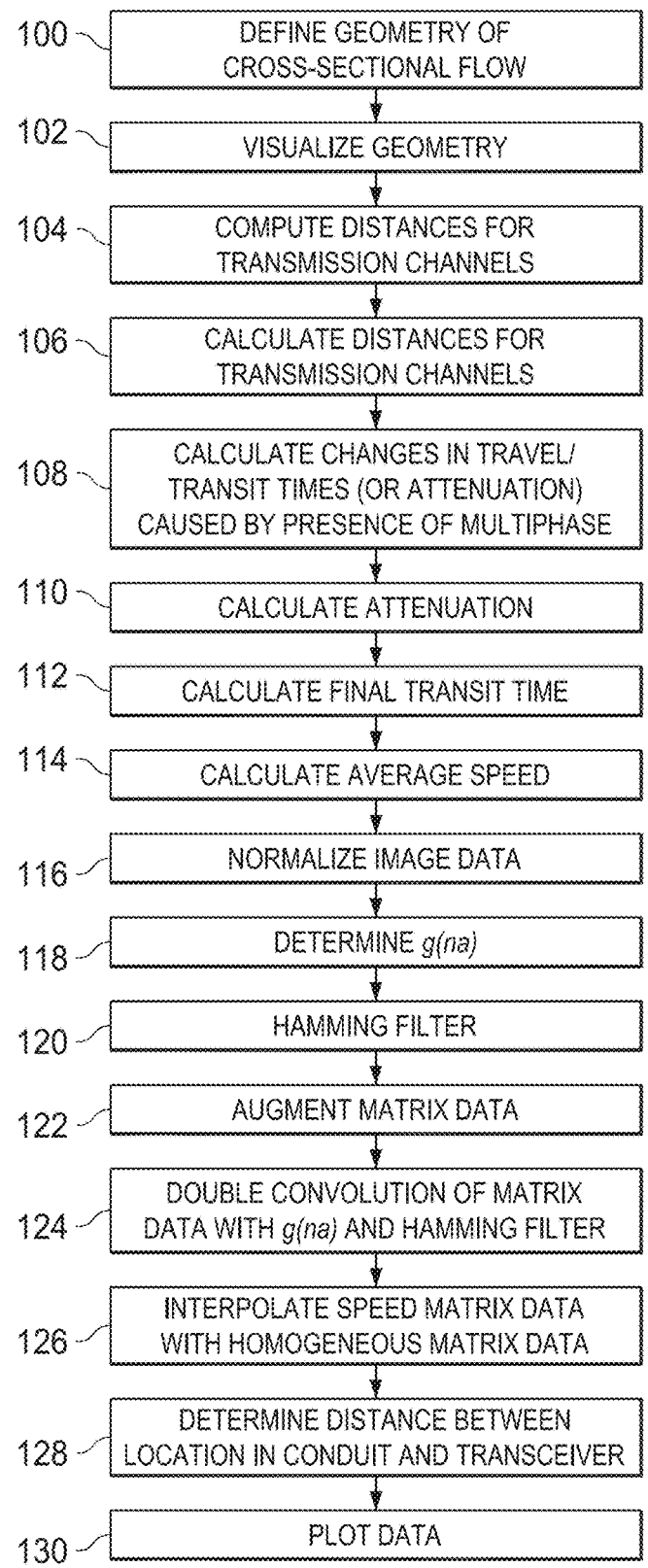
FIG. 13 is a functional block diagram of a set of steps performed in tomographic reconstruction of multiphase flow performed in accordance with the present invention.
Figure 14:
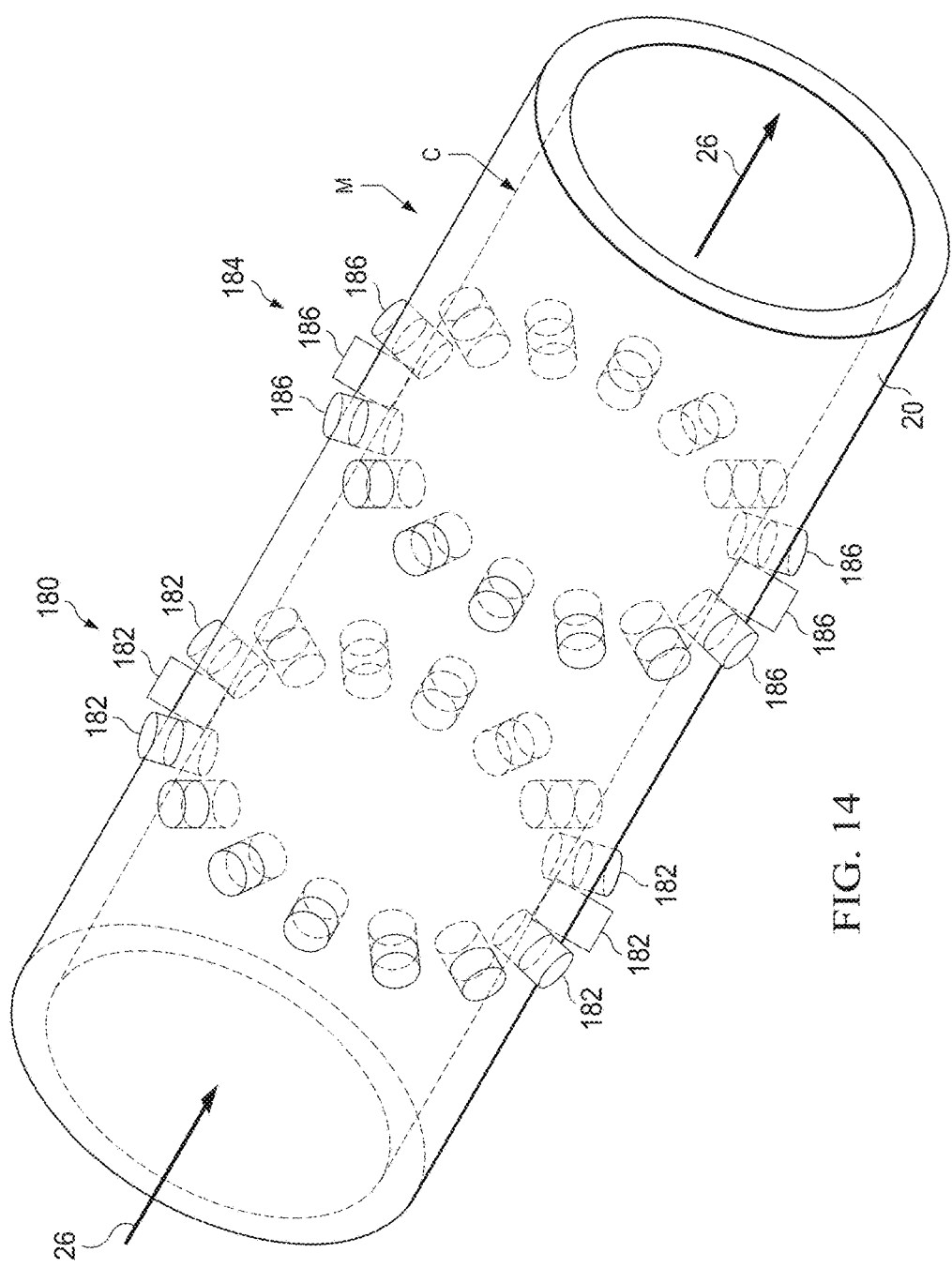
FIG. 14 is an isometric view, partially in schematic diagram form, of a multichannel ultrasonic imaging system mounted with a conduit according to the present invention.

A structural implementation analogous to the 3 phase reconstruction methodology by synthesization of FIG. 13 is contemplated according to the present invention. As shown in FIG. 14, a two (or more) channel version of the tomographic data acquisition system T shown in FIG. 1 may be provided. As shown in FIG. 14, a multi-channel data acquisition system M may be provided with an example array 180 is formed of transceivers 182 deployed circumferentially around the periphery of the tubing 24. The transceivers 182 provide ultrasonic energy at a frequency such as in the range of from 100 to 800 kHz which permits very good resolution, particularly in the measurement of speed of sound in oil-water flows. In the present example, an ultrasonic frequency of 333 kHz is used in transducer array 180. However, energy in these ranges is heavily attenuated by the presence of gas.

Therefore, with the present invention a second array 184 of transceivers 186 is deployed circumferentially around the periphery of the tubing 24. The transceivers 186 provide ultrasonic energy at a frequency such as in the range of from 20 to 100 kHz which has lower resolution, but penetrates through gas more effectively resulting in improved images for gas phases. In the present example, an ultrasonic frequency of 40 kHz is used in transducer array 184.

Each array 180 and 184 could provide data for independent processing according to the techniques of FIG. 12. Alternatively, the combination methodology of FIG. 13 could be directly applied to each of the output images of the sensor arrays 180 and 184 to generate a better image of 3 phase flow.

Optimized System for Geometric Reconstruction

In general it is preferable with the present invention to utilize a general purpose microprocessor for computation, particularly those for the application of the processing methodology of FIGS. 12 and 13. In order to implement the geometric resolution algorithm of FIG. 15, the present invention also contemplates thresholding the input data into digital form and implementing the processing by the data processing system D through synchronous digital logic. Another approach contemplated is to implement the processing by the data processing system D in a field programmable gate array (FPGA) or specifically designed integrated circuit (IC). The computational overhead is then massively reduced allowing a lower power system to operate, more suited for downhole conditions.

Data Processing System

Figure 16:
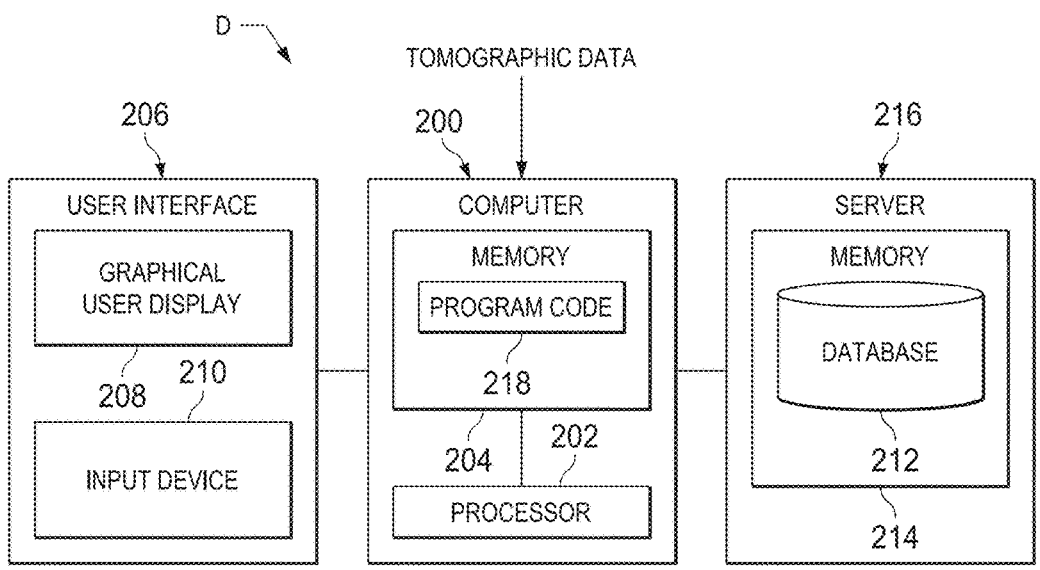
FIG. 16 is a schematic diagram of a data processing system for tomographic reconstruction of multiphase flow performed in accordance with the present invention.

As illustrated in FIG. 16, the data processing system D according to the present invention includes a computer 200 having a processor 202 and memory 204 coupled to the processor 202 to store operating instructions, control information and database records therein. The computer 200 may, if desired, be a Linux cluster such as is available from HP Corporation or other source, a multicore processor with nodes such as those from IBM, Intel Corporation or Advanced Micro Devices (AMD), or a mainframe computer of any conventional type of suitable processing capacity such as those available from IBM, or other source.

It should be noted that other digital processors, may be used, such as personal computers in the form of a laptop computer, notebook computer or other suitable programmed or programmable digital data processing apparatus.

The computer 200 has a user interface 206 and an output display 208 for displaying output data or records according to the present invention to form tomographic images of multiphase flow in conduits based on tomographic data from the transducer arrays U or M. The output display 208 includes components such as a printer and an output display screen capable of providing printed output information or visible displays in the form of graphs, data sheets, graphical images, data plots and the like as output records or images.

The user interface 206 of computer 200 also includes a suitable user input device or input/output control unit 210 to provide a user access to control or access information and database records and operate the computer 200. The input/output control unit 210 also may receive data measurements of flow obtained during data acquisition in the manner described above. Data processing system D further includes a database 212 stored in memory, which may be internal memory 204, or an external, networked, or non-networked memory as indicated at 214 in an associated database server 216.

The data processing system D includes program code 218 stored in non-transitory memory 204 of the computer 200. The program code 218, according to the present invention is in the form of computer operable instructions causing the data processor 202 to form tomographic images of multiphase flow in conduits, as has been set forth.

It should be noted that program code 218 may be in the form of microcode, programs, routines, or symbolic computer operable languages that provide a specific set of ordered operations that control the functioning of the data processing system D and direct its operation. The instructions of program code 218 may be stored in non-transitory form in memory 204 of the computer 200, or on computer diskette, magnetic tape, conventional hard disk drive, electronic read-only memory, optical storage device, or other appropriate data storage device having a non-transitory computer usable medium stored thereon. Program code 218 may also be contained on a data storage device such as server 214 as a non-transitory computer readable medium, as shown.

The invention has been sufficiently described so that a person with average knowledge in the matter may reproduce and obtain the results mentioned in the invention herein Nonetheless, any skilled person in the field of technique, subject of the invention herein, may carry out modifications not described in the request herein, to apply these modifications to a determined structure, or in the manufacturing process of the same, requires the claimed matter in the following claims; such structures shall be covered within the scope of the invention.

It should be noted and understood that there can be improvements and modifications made of the present invention described in detail above without departing from the spirit or scope of the invention as set forth in the accompanying claims.

What is claimed is:

1. An apparatus for forming a tomographic image of relative presence and position of oil, gas and water phases of three phase flow over a cross-sectional area of a conduit, comprising:
   an array of a plurality of transmitters mounted about the periphery of the conduit and emitting energy to travel over transmission channels from individual ones of the transmitters through the three phase flow in the conduit;
   an array of a plurality of receivers mounted about the periphery of the conduit, each receiving energy after travel over the transmission channels from the individual ones of the plurality of transmitters through the three phase flow in the conduit; and
   a data processing system forming the tomographic image of the three phase flow in the conduit based on travel of the energy over the transmission channels from the individual ones of the plurality of transmitters to each of the plurality of receivers through the three phase flow in the conduit, comprising:
   (1) a processor forming measures of the speed of travel of the energy in the three phase flow over the transmission channels from the individual ones of the plurality of transmitters to each of the plurality of receivers;
   (2) the processor further forming measures of the attenuation of the energy in the three phase flow over the transmission channels from the individual ones of the plurality of transmitters to each of the plurality of receivers;
   (3) the processor further forming a synthesized composite image as the tomographic image of the relative presence and position of the oil, gas and water phases over the cross-sectional area of the conduit based on the formed measures of the speed of travel and attenuation of the energy in the three phase flow in the conduit between individual ones of the plurality of transmitters to each of the plurality of receivers; and
   (4) a display presenting the synthesized composite image as the tomographic image of the relative presence and position of the oil, gas and water phases over the cross-sectional area of the conduit for evaluation and analysis.

2. The apparatus of claim 1, further including the data processing system comprising:
   a memory storing the synthesized composite image formed by the processor.

3. The apparatus of claim 1, wherein the plurality of transmitters and plurality of receivers are formed by transceivers.

4. The apparatus of claim 1, wherein the energy emitted by the plurality of transmitters and received by the plurality of receivers comprises ultrasonic energy.

5. A data processing system forming a tomographic image of relative presence and position of oil, gas and water phases of three phase flow over a cross-sectional area of a conduit based on energy travel through the three phase flow in the conduit over transmission channels from individual ones of an array of a plurality of receivers mounted about the periphery of the conduit to a plurality of receivers mounted about the periphery of the conduit, each of the plurality of receivers receiving energy after travel over the transmission channels from the individual ones of the plurality of transmitters, the data processing system comprising:

(a) a processor forming measures of the speed of travel of the energy in the three phase flow over the transmission channels from the individual ones of the plurality of transmitters to each of the plurality of receivers;

(b) the processor further forming measures of the attenuation of the energy in the three phase flow over the transmission channels from the individual ones of the plurality of transmitters to each of the plurality of receivers;

(c) the processor further forming a synthesized composite image as the tomographic image of the relative presence and position of the oil, gas and water phases over the cross-sectional area of the conduit based on the formed measures of the speed of travel and attenuation of the energy in the three phase flow in the conduit between individual ones of the plurality of transmitters to each of the plurality of receivers; and (d) a display presenting the synthesized composite image as the tomographic image of the relative presence and position of the oil, gas and water phases over the cross-sectional area of the conduit for evaluation and analysis.

6. The data processing system of claim 5, further including:

a memory storing the synthesized composite image formed by the processor.

7. An apparatus for forming a tomographic image of relative presence and position of oil, gas and water phases of three phase flow over a cross-sectional area of a conduit, comprising:

(a) an array of a plurality of transmitters mounted about the periphery of the conduit and emitting energy to travel over transmission channels from individual ones of the transmitters through the three phase flow in the conduit;

(b) an array of a plurality of receivers mounted about the periphery of the conduit, each receiving energy after travel over the transmission channels from the individual ones of the plurality of transmitters through the three phase flow in the conduit; and (c) a data processing system forming the tomographic image of the three phase flow in the conduit based on travel of the energy over the transmission channels from the individual ones of the plurality of transmitters to each of the plurality of receivers through the three phase flow in the conduit, comprising:

(1) a processor forming measures of the speed of travel of the energy in the three phase flow over the transmission channels from the individual ones of the plurality of transmitters to each of the plurality of receivers;

(2) the processor further forming measures of the attenuation of the energy in the three phase flow over the transmission channels from the individual ones of the plurality of transmitters to each of the plurality of receivers;

(3) the processor further forming a geometrically reconstructed composite image as the tomographic image of the relative presence and position of the oil, gas and water phases over the cross-sectional area of the conduit based on the formed measures of the speed of travel and attenuation of the energy in the three phase flow in the conduit between individual ones of the plurality of transmitters to each of the plurality of receivers; and (4) a display presenting the geometrically reconstructed image as the tomographic image of the relative presence and position of the oil, gas and water phases over the cross-sectional area of the conduit for evaluation and analysis.

8. The apparatus of claim 7, further including the data processing system comprising:

a memory storing the geometrically reconstructed composite image formed by the processor.

9. The apparatus of claim 7, wherein the plurality of transmitters and plurality of receivers are formed by transceivers.

10. The apparatus of claim 7, wherein the energy emitted by the plurality of transmitters and received by the plurality of receivers comprises ultrasonic energy.

11. A data processing system forming a tomographic image of relative presence and position of oil, gas and water phases of three phase flow over a cross-sectional area of a conduit based on energy travel through the fluid in the conduit over transmission channels from individual ones of an array of a plurality of receivers mounted about the periphery of the conduit to a plurality of receivers mounted about the periphery of the conduit, each of the plurality of receivers receiving energy after travel over the transmission channels from the individual ones of the plurality of transmitters, the data processing system comprising:

(a) a processor forming measures of the speed of travel of the energy in the three phase flow over the transmission channels from the individual ones of the plurality of transmitters to each of the plurality of receivers;

(b) the processor further forming measures of the attenuation of the energy in the three phase flow over the transmission channels from the individual ones of the plurality of transmitters to each of the plurality of receivers;

(c) the processor further forming a geometrically reconstructed composite image as the tomographic image of the relative presence and position of the oil, gas and water phases over the cross-sectional area of the conduit based on the formed measures of the speed of travel and attenuation of the energy in the three phase flow in the conduit between individual ones of the plurality of transmitters to each of the plurality of receivers; and (d) a display presenting the geometrically reconstructed composite image as the tomographic image of the relative presence and position of the oil, gas and water phases over the cross sectional area of the conduit for evaluation and analysis.

12. The data processing system of claim 11, further including:

a memory storing the geometrically reconstructed composite image formed by the processor.

* * * * *